US008603790B2

(12) United States Patent
Deisseroth et al.

(10) Patent No.: US 8,603,790 B2
(45) Date of Patent: Dec. 10, 2013

(54) SYSTEMS, METHODS AND COMPOSITIONS FOR OPTICAL STIMULATION OF TARGET CELLS

(75) Inventors: Karl Deisseroth, Palo Alto, CA (US); Feng Zhang, Cambridge, MA (US); Viviana Gradinaru, Menlo Park, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 122 days.

(21) Appl. No.: 12/988,567

(22) PCT Filed: Apr. 8, 2009

(86) PCT No.: PCT/US2009/039949
§ 371 (c)(1),
(2), (4) Date: Dec. 7, 2010

(87) PCT Pub. No.: WO2009/131837
PCT Pub. Date: Oct. 29, 2009

(65) Prior Publication Data
US 2011/0105998 A1 May 5, 2011

Related U.S. Application Data

(60) Provisional application No. 61/047,219, filed on Apr. 23, 2008.

(51) Int. Cl.
| C12N 13/00 | (2006.01) |
| C12N 1/20 | (2006.01) |
| C12N 15/00 | (2006.01) |
| C12N 5/00 | (2006.01) |
| C12N 5/02 | (2006.01) |
| C12Q 1/02 | (2006.01) |
| A61F 5/00 | (2006.01) |

(52) U.S. Cl.
USPC .... 435/173.1; 435/29; 435/252.3; 435/320.1; 435/325; 435/375; 435/471; 604/20

(58) Field of Classification Search
None
See application file for complete search history.

(56) References Cited

U.S. PATENT DOCUMENTS

| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Land et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,939,320 A | 8/1999 | Littman et al. |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |

(Continued)

FOREIGN PATENT DOCUMENTS

| EP | 1 334 748 | 8/2003 |
| JP | 2006-295350 | 10/1994 |

(Continued)

OTHER PUBLICATIONS

Banghart et al. "Engineering Light-Gated Ion Channels" Biochemistry 2006 45(51), 15129-15141.*
Zhang F, et al. Nature 446:633-639, Apr. 5, 2007.*
Gradinaru V, et al. Science 324:354-359, Apr. 17, 2009.*
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga *Volvox carteri*", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.

(Continued)

*Primary Examiner* — Robert Landsman
(74) *Attorney, Agent, or Firm* — Paula A. Borden; Bozicevic, Field & Francis LLP.

(57) ABSTRACT

Methods, systems and devices are implemented in connection with light-responsive ion channel molecules. One such method is implemented using a light-activated ion channel molecule that responds to a light stimulus. The method includes engineering the light-activated ion channel molecule in a cell; and activating the ion channel molecule, in response to light stimulus that is provided to the ion channel molecule and that has properties that do not activate a ChR2 ion channel, to allow ions to pass through the light-activated ion channel molecule.

14 Claims, 19 Drawing Sheets

(56) References Cited

U.S. PATENT DOCUMENTS

| | | |
|---|---|---|
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et |
| 7,313,442 B2 | 12/2007 | Velasco et al. |
| 7,603,174 B2 | 10/2009 | De Ridder |
| 7,613,520 B2 | 11/2009 | De Ridder |
| 7,686,839 B2 | 3/2010 | Parker |
| 7,824,869 B2 | 11/2010 | Hegemann et al. |
| 2002/0094516 A1 | 7/2002 | Calos et al. |
| 2002/0155173 A1 | 10/2002 | Chopp et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0034882 A1 | 2/2004 | Vale et al. |
| 2004/0039312 A1 | 2/2004 | Hillstead et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0155348 A1 | 7/2006 | De Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0145418 A1 | 6/2010 | Zhang et al. |
| 2010/0190229 A1 | 7/2010 | Zhang et al. |
| 2010/0234273 A1 | 9/2010 | Boyden et al. |
| 2011/0112179 A1 | 5/2011 | Deisseroth et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0166632 A1 | 7/2011 | Deisseroth et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0253261 A1 | 10/2012 | Poletto et al. |

FOREIGN PATENT DOCUMENTS

| | | |
|---|---|---|
| WO | WO 01-25466 | 4/2001 |
| WO | WO 03/106486 A2 | 2/2003 |
| WO | WO 03-040323 | 5/2003 |
| WO | WO 03-084994 | 10/2003 |
| WO | WO 03-102156 | 12/2003 |
| WO | WO 2007-024391 | 3/2007 |
| WO | WO 2007-131180 | 11/2007 |
| WO | WO 2009-131837 | 10/2009 |
| WO | WO 2010/011404 A3 | 1/2010 |
| WO | WO 2011/066320 A3 | 6/2011 |
| WO | WO 2011-116238 A2 | 9/2011 |
| WO | WO 2011/127088 A3 | 10/2011 |
| WO | WO2012/061681 | 5/2012 |
| WO | WO2012/061684 | 5/2012 |

(56) References Cited

FOREIGN PATENT DOCUMENTS

| WO | WO2012/061688 | 5/2012 |
|---|---|---|
| WO | WO2012/061690 | 5/2012 |
| WO | WO 2012/134704 A2 | 10/2012 |

OTHER PUBLICATIONS

Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a Natronomonas Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of *Volvox carteri* are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
McAllister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
U.S. Appl. No. 13/299,727, filed Nov. 18, 2011, Lee, et al.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Gold, et al. "Representation of a perceptual decision in developing oculomotor commands", Nature, 2000, vol. 404, pp. 390-394.
Gregory, et al. "Integration site for *Streptomyces* phage φBT1 and development of site-specific integrating vectors", Journal of Bacteriology, 2003, vol. 185, No. 17, pp. 5320-5323.
Gulick, et al. "Transfection using DEAE-Dextran" Supplement 40, Current Protocols in Molecular Biology, 1997, Supplement 40, 9.2.1-9.2.10.

Hausser, et al. "Tonic Synaptic Inhibition Modulates Neuronal Output Pattern and Spatiotemporal Synaptic Integration", Neuron, 1997, vol. 19, pp. 665-678.
Kingston et al. "Transfection and Expression of Cloned DNA," Supplement 31, Current Protocols in Immunology, 1999, 10.13.1-10.13.9.
Louis et al. "Cloning and sequencing of the cellular-viral junctions from the human adenovirus type 5 transformed 293 cell line," Virology, 1997, vol. 233, pp. 423-429.
Mortensen et al. "Selection of Transfected Mammalian Cells," Supplement 86, Current Protocols in Molecular Biology, 1997, 9.5.1-09.5.19.
Pear "Transient Transfection Methods for Preparation of High-Titer Retroviral Supernatants" Supplement 68, Current Protocols in Molecular Biology, 1996, 9.11.I-9.11.I 8.
Pouille, et al. "Routing of spike series by dynamic circuits in the hippocampus", Nature, 2004, vol. 429: pp. 717-723.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Wells et al. "Application of Infrared light for in vivo neural stimulation," Journal of Biomedical Optics, 2005, vol. 10(6), pp. 064003-1-064003-12.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila* rhodopsin cytoplasmic tail domain is required for maintenance of rhabdomere structure." The FASEB Journal, 2007, vol. 21, p. 449-455.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.

(56) References Cited

OTHER PUBLICATIONS

Bocquet et al. "A prokaryotic proton-gated ion channel from the nicotinic acetylcholine receptor family." Nature Letters, 2007, vol. 445, p. 116-119.

Boyden, et al. "Millisecond-timescale, genetically targeted optical control of neural activity" Nature Neuroscience, 2005, vol. 8, No. 9: pp. 1263-1268.

Bi, et al. "Ectopic Expression of a Microbial-Type Rhodopsin Restores Visual Responses in Mice with Photoreceptor Degeneration", Neuron, 2006, vol. 50, No. 1: pp. 23-33.

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.

Blomer et al., "Highly Efficient and Sustained Gene Transfer in Adult Neurons with *Lentivirus* Vector", Journal of Virology,1997, vol. 71, No. 9: pp. 6641-6649.

Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-7.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

Brown, et al. "Long-term potentiation induced by θ frequency stimulation is regulated by a protein phosphate-operated gate." The Journal of Neuroscience, 2000, vol. 20, No. 21, pp. 7880-7887.

Callaway, et al. "Photostimulation using caged glutamate reveals functional circuitry in living brain slices", Proc. Natl. Acad. Sci. USA., 1993, vol. 90: pp. 7661-7665.

Campagnola et al. "Fiber-coupled light-emitting diode for localized photostimulation of neurons expressing channelrhodopsin-2." Journal of Neuroscience Methods , 2008, vol. 169, Issue 1. Abstract only.

Cenatiempo "Prokaryotic gene expression in vitro: transcription-translation coupled systems", Biochimie, 1986, vol. 68(4): pp. 505-515.

Claudio et al. "Nucleotide and deduced amino acid sequences of *Torpedo californica* acetylcholine receptor gamma subunit." PNAS USA,1983, vol. 80, p. 1111-1115.

Collingridge et al. "Inhibitory post-synaptic currents in rat hippocampal CA1 neurones." J. Physiol., 1984, vol. 356, pp. 551-564.

Covington, et al. "Antidepressant Effect of Optogenetic Stimulation of the Medial Prefrontal Cortex." Journal of Neuroscience, 2010, vol. 30(48), pp. 16082-16090.

Crouse, et al. "Expression and amplification of engineered mouse dihydrofolate reductase minigenes" Mol. Cell. Biol. , 1983, vol. 3(2): pp. 257-266.

Cucchiaro et al., "*Phaseolus vulgaris* leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cucchiaro et al., "Electron-Microsoft Analysis of Synaptic Input from the Perigeniculate Nucleus to A-Lamine of the Lateral Geniculate Nucleus in Cats", The Journal of Comparative Neurology, 1991, vol. 310, pp. 316-336.

Cui, et al., "Electrochemical deposition and characterization of conducting polymer polypyrrole/PSS on multichannel neural probes," Sensors and Actuators, 2001, vol. 93(1): pp. 8-18.

Date, et al. "Grafting of Encapsulated Dopamine-Secreting Cells in Parkinson's Disease: Long-Term Primate Study", Cell Transplant, 2000, vol. 9, pp. 705-709.

Dalva, et al. "Rearrangements of Synaptic Connections in Visual Cortex Revealed by Laser Photostimulation", Science, 1994,vol. 265, pp. 255-258.

Dederen, et al. "Retrograde neuronal tracing with cholera toxin B subunit: comparison of three different visualization methods", Histochemical Journal, 1994, vol. 26, pp. 856-862.

Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

Deisseroth et al., "Translocation of Calmodulin to the Nucleus Supports CREB Phosphorylation in Hippocampal Neurons", Nature, 1998, vol. 392, pp. 198-202.

Deisseroth et al., "Signaling from Synapse to Nucleus: the logic Behind the Mechanisms", Currrent Opinion in Neurobiology, 2003, vol. 13, pp. 354-365.

Deisseroth "Next-generation optical technologies for illuminating genetically targeted brain circuits," The Journal of Neuroscience, 2006, vol. 26, No. 41, pp. 10380-10386.

Denk, W., et al. "Anatomical and functional imaging of neurons using 2-photon laser scanning microscopy", Journal of Neuroscience Methods, 1994, vol. 54, pp. 151-162.

Ditterich, et al. "Microstimulation of visual cortex affects the speed of perceptual decisions", 2003, Nature Neuroscience, vol. 6, No. 8, pp. 891-898.

Dittgen, et al. "*Lentivirus*-based genetic manipulations of cortical neurons and their optical and electrophysiological monitoring in vivo", PNAS, 2004, vol. 101, No. 52, pp. 18206-18211.

Ensell, et al. "Silicon-based microelectrodes for neurophysiology, micromachined from silicon-on-insulator wafers," Med. Biol. Eng. Comput., 2000, vol. 38, pp. 175-179.

Eisen, "Treatment of amyotrophic lateral sclerosis", Drugs Aging, 1999; vol. 14, No. 3, pp. 173-196.

Evanko "Optical excitation yin and yang" Nature Methods, 2007, 4:384.

Esposito et al. "The integrase family of tyrosine recombinases: evolution of a conserved active site domain" , Nucleic Acids Research, 1997, vol. 25, No. 18, pp. 3605-3614.

Fabian et al. "Transneuronal transport of lectins" Brain Research, 1985, vol. 344, pp. 41-48.

Falconer et al. "High-throughput screening for ion channel modulators," Journal of Biomolecular Screening, 2002, vol. 7, No. 5, pp. 460-465.

Farber, et al. "Identification of Presynaptic Neurons by Laser Photostimulation", Science, 1983, vol. 222, pp. 1025-1027.

Feng, et al. "Imaging Neuronal Subsets in Transgenic Mice Expressing Multiple Spectral Variants of GFP", Neuron, 2000, vol. 28, pp. 41-51.

Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.

Fitzsimons et al., "Promotors and Regulatory Elements that Improve Adeno-Associated Virus Transgene Expression in the Brain", 2002, Methods, vol. 28, pp. 227-236.

Foster, "Bright blue times", Nature, 2005, vol. 433, pp. 698-699.

Gelvich et al. "Contact flexible microstrip applicators (CFMA) in a range from microwaves up to short waves," IEEE Transactions on Biomedical Engineering, 2002, vol. 49, Issue 9: 1015-1023.

Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.

Gilman, et al al. "Isolation of sigma-28-specific promoters from *Bacillus subtilis* DNA" Gene, 1984, vol. 32(1-2): pp. 11-20.

Glick et al."Factors affecting the expression of foreign proteins in *Escherichia coli*", Journal of Industrial Microbiology, 1987, vol. 1(5): pp. 277-282.

Goekoop, R. et al. "Cholinergic challenge in Alzheimer patients and mild cognitive impairment differentially affects hippocampal activation—a pharmacological fMRI study." Brain, 2006, vol. 129, pp. 141-157.

Gordon, et al. "Regulation of Thy-1 Gene Expression in Transgenic Mice", Cell, 1987, vol. 50, pp. 445-452.

Gorelova et al. , "The course of neural projection from the prefrontal cortex to the nucleus accumbens in the rat ", Neuroscience, 1997, vol. 76, No. 3, pp. 689-706.

Gottesman et al."Bacterial regulation: global regulatory networks," Ann. Rev. Genet. , 1984, vol. 18, pp. 415-441.

(56) References Cited

OTHER PUBLICATIONS

Greenberg, et al. "Three-year outcomes in deep brain stimulation for highly resistant obsessive-compulsive disorder," Neuropsychopharmacology, 2006, vol. 31, pp. 2384-2393.

Groth et al. "Phage integrases: biology and applications," Journal of Molecular Biology, 2004, vol. 335, pp. 667-678.

Groth, et al. "A phage integrase directs efficient site-specific integration in human cells", PNAS, 2000, vol. 97, No. 11, pp. 5995-6000.

Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.

Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.

Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.

Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.

Hegemann et al., "All-trans Retinal Constitutes the Functional Chromophore in *Chlamydomonas* rhodopsin", Biophys. J. , 1991, vol. 60, pp. 1477-1489.

Herry, et al. "Switching on and off fear by distinct neuronal circuits," Nature, 2008, vol. 454, pp. 600-606.

Hildebrandt et al, "Bacteriorhodopsin expressed in *Schizosaccharomyces pombe* pumps protons through the plasma membrane," PNAS, 1993, vol. 90, pp. 3578-3582.

Hirase, et al. "Multiphoton stimulation of neurons", J Neurobiol, 2002, vol. 51, No. 3: pp. 237-247.

Hodaie, et al., "Chronic Anterior Thalamus Stimulation for Intractable Epilepsy," Epilepsia, 2002, vol. 43, pp. 603-608.

Hoffman et al., "K+ Channel Regulation of Signal Propagation in Dendrites of Hippocampal Pyramidal Neurons", 1997, Nature, vol. 387: pp. 869-874.

Hosokawa, T. et al. "Imaging spatio-temporal patterns of long-term potentiation in mouse hippocampus." Philos. Trans. R. Soc. Lond. B., 2003, vol. 358, pp. 689-693.

Hynynen, et al. "Clinical applications of focused ultrasound—The brain." Int. J. Hyperthermia, 2007, vol. 23, No. 2: pp. 193-202.

International Search Report for International Application No. PCT/US2009/053474, dated Oct. 8, 2009.

Isenberg et al. "Cloning of a Putative Neuronal Nicotinic Aceylcholine Receptor Subunit," Journal of Neurochemistry, 1989, pp. 988-991.

Johnston et al. "Isolation of the yeast regulatory gene *GAL4* and analysis of its dosage effects on the galactose/melibiose regulon," PNAS, 1982, vol. 79, pp. 6971-6975.

Kandel, E.R.,et al. "Electrophysiology of Hippocampal Neurons: I. Sequential Invasion and Synaptic Organization," J Neurophysiol, 1961, vol. 24, pp. 225-242.

Kandel, E.R.,et al. "Electrophysiology of Hippocampal Neurons: II. After-Potentials and Repetitive Firing", J Neurophysiol., 1961, vol. 24, pp. 243-259.

Karreman et al. "On the use of double FLP recognition targets (FRTs) in the LTR of retroviruses for the construction of high producer cell lines" , Nucleic Acids Research, 1996, vol. 24, No. 9: pp. 1616-1624.

Kato et al. "Present and future status of noninvasive selective deep heating using RF in hyperthermia." Med & Biol. Eng. & Comput 31 Supp: S2-11, 1993. Abstract. p. S2 only.

Katz, et al. "Scanning laser photostimulation: a new approach for analyzing brain circuits," Journal of Neuroscience Methods, 1994, vol. 54, pp. 205-218.

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khossravani et al., "Voltage-Gated Calcium Channels and Idiopathic Generalized Epilepsies", Physiol. Rev., 2006, vol. 86: pp. 941-966.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kingston et al. "Transfection of DNA into Eukaryotic Cells," Supplement 63, Current Protocols in Molecular Biology, 1996, 9.1.1-9.1.11, 11 pages.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitayama, et al. "Regulation of neuronal differentiation by *N*-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Landy, A. "Mechanistic and structural complexity in the site-specific recombination pathways of Int and FLP", Current Opinion in Genetics and Development, 1993, vol. 3, pp. 699-707.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Lee et al., "Potassium Channel Gone Therapy Can Prevent Neuron Deatch Resulting from Necrotic and Apoptotic Insults", Journal of Neurochemistry, 2003, vol. 85: pp. 1079-1088.

Levitan et al. "Surface Expression of Kv1 Voltage-Gated K+ Channels Is Governed by a C-terminal Motif," Trends Cardiovasc. Med., 2000, vol. 10, No. 7, pp. 317-320.

Li et al. "Fast noninvasive activation and inhibition of neural and network activity by vertebrate rhodopsin and green algae channelrhodopsin." PNAS, 2005, vol. 102, No. 49, p. 17816-17821.

Lim et al., "A Novel Targeting Signal for Proximal Clustering of the Kv2.1K+ Channel in Hippocampal Neurons", Neuron, 2000, vol. 25: pp. 385-397.

Lima, et al. "Remote Control of Behavior through Genetically Targeted Photostimulation of Neurons", Cell, 2005, vol. 121: pp. 141-152.

Liman, et al. "Subunit Stoichiometry of a Mammalian K+ Channel Determined by Construction of Multimeric cDNAs," Neuron, 1992,vol. 9, pp. 861-871.

Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of *FRT* sites in the maize genome," Nucleic Acids Research , 1996, vol. 24, No. 19: pp. 3784-3789.

Ma et al. "Role of ER Export Signals in Controlling Surface Potassium Channel Numbers," Science, 2001, vol. 291, pp. 316-319.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mattson, "Apoptosis in Neurodegenerative Disorders", Nature Reviews, 2000, vol. 1: pp. 120-129.

(56) References Cited

OTHER PUBLICATIONS

Mayberg et al. "Deep Brain Stimulation for Treatment-Resistant Depression," Focus, 2008, vol. VI, No. 1, pp. 143-154.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Nacher, et al. "NMDA receptor antagonist treatment increases the production of newneurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration,"Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.11.I -9.11.I 8.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Qiu et al. "Induction of photosensitivity by heterologous expression of melanopsin", Nature, 2005, vol. 433: pp. 745-749.
Rathnasingham et al., "Characterization of implantable microfabricated fluid delivery devices," IEEE Transactions on Biomedical Engineering, 2004, vol. 51, No. 1: pp. 138-145.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast *GAL4* gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.

(56) References Cited

OTHER PUBLICATIONS

Stoll, et al. "Phage TP901-I site-specific integrase functions in human cells," Journal of Bacteriology, 2002, vol. 184, No. 13: pp. 3657-3663.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:19.1-19.39.
Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating *Lentivirus* Vector for Safe and Efficient In Vivo Gene Delivery", Journal of Virology, 1998, vol. 72, No. 12, pp. 9873-9880.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers"Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Gonzalez, et al., "Cell-Based Assays and Instrumentation for Screening Ion-Channel Targets", DDT, 1999, vol. 4, No. 9, pp. 431439.
Natochin, et al. "Probing rhodopsin-transducin interaction using *Drosophila* Rh1-bovine rhodopsin chimeras,"Vision Res., 2006, vol. 46, No. 27: pp. 4575-4581.
Peterlin, et al. "Optical probing of neuronal circuits with calcium indicators," PNAS, 2000, vol. 97, No. 7: pp. 3619-3624.
Tye, et al. "Optogenetic investigation of neural circuits underlying brain disease in animal models," Nature Reviews Neuroscience (Mar. 2012), 13(4):251-266.
Gradinaru, et al., Molecular and Cellular Approaches for Diversifying and Extending Optogenetics, Cell, 2010, vol. 141, No. 1, pp. 154-165.

(56) References Cited

OTHER PUBLICATIONS

RecName: Full=Halorhodopsin; Short=HR; Alt Name: Full=NpHR; XP002704922, retrieved from EBI accession No. UNIPROT: P15647. Database accession No. P15647. Apr. 1, 1990.

"*N. pharaonis* halorhodopsin (hop) gene, complete cds.", XP002704883, retrieved from EBI accession No. EMBL: J05199. Database accession No. J05199. Nov. 22, 1990.

"Subname: Fluu= Bacteriorhodopsin"; XP002704863, retrieved from EBI accession No. UNIPROT: B0R5N9. Database accession No. B0R5N9. Apr. 8, 2008.

Zhang, et al., "The Microbial Opsin Family of Optogenetic Tools", Cell, 2011, vol. 147, No. 7, pp. 1146-1457.

Balint, et al., "The Nitrate Transporting Photochemical Reaction Cycle of the *pharaonis* Halorhodopsin", Biophysical Journal, 2004, vol. 86, pp. 1655-1663.

\* cited by examiner a

FIG. 1B

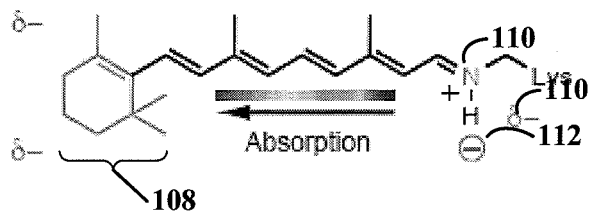

```
ChR2    M.......... ......DYGG ALSAVG.... .......... .......REL  14
ChR1    MSRRPWLLAL ALAVALAAGS AGASTGSDAT VPVATQDGPD YVFHRAHERM  50
VChR1   M.......... ......DY.. .......... .......... .....PVARS   8

ChR2    LFVTNPVVVN .GSVLVP..E DQCYCAGWIE SRGTNGAQTA SNVLQWLAAG  61
ChR1    LFQTSYTLEN NGSVICIPNN GQCFCLAWLK SNGTNAEKLA ANILQWITFA 100
VChR1   LIVRYPTDLG NGTVCMP..R GQCYCEGWLR SRGTSIEKTI AITLQWVVFA  56
                                                    ═══TM1═══

ChR2    FSILLLMFYA YQTWKSTCGW EEIYVCAIEM VKVILEFFFE FKNPSMLYLA 111
ChR1    LSALCLMFYG YQTWKSTCGW EEIYVATIEM IKFIIEYFHE FDEPAVIYSS 150
VChR1   LSVACLGWYA YQAWRATCGW EEVYVALIEM MKSIIEAFHE FDSPATLWLS 106
        ═       ═══════TM2═══
          ⌒102 ⌒104⌒104
ChR2    TGHRVQWLRY AEWLLTCPVI LIHLSNLTGL SNDYSRRTMG LLVSDIGTIV 161
ChR1    NGNKTVWLRY AEWLLTCRVI LIHLSNLTGL ANDYNKRTMG LLVSDIGTIV 200
VChR1   SGNGVVWMRY GEWLLTCPVL LIHLSNLTGL KDDYSKRTMG LLVSDVGCIV 156
        ═══════TM3═══════            ═══════TM4══
                              ⌒106
ChR2    WGATSAMATG YVKVIFFCLG LCYGANTFFH AAKAYIEGYH TVPKGRCRQV 211
ChR1    WGTTAALSKG YVRVIFFLMG LCYGIYTFFN AAKVYIEAYH TVPKGICRDL 250
VChR1   WGATSAMCTG WTKILFFLIS LSYGMYTYFH AAKVYIEAFH TVPKGICREL 206
                     ═══════TM5═══════
                              ⌒102      ⌒102     ⌒104⌒106
ChR2    VTGMAWLFFV SWGMFPILFI LGPEGFGVLS VYGSTVGHTI IDLMSKNCWG 261
ChR1    VRYLAWLYFC SWAMFPVLFL LGPEGFGHIN QFNSAIAHAI LDLASKNAWS 300
VChR1   VRVMAWTFFV AWGMFPVLFL LGTEGFGHIS PYGSAIGHSI LDLIAKNMWG 256
        ═══TM6═══                               ═══TM7═══

ChR2    LLGHYLRVLI HEHILIHGDI RKTTKLNIGG TEIEVETLVE DEAE       311
ChR1    MMGHFLRVKI HEHILLYGDI RKKQKVNVAG QEMEVETMVH EEDD       350
VChR1   VLGNYLRVKI HEHILLYGDI RKKQKITIAG QEMEVETLVA EEED       306
        ═════════
```

SYSTEMS, METHODS AND COMPOSITIONS FOR OPTICAL STIMULATION OF TARGET CELLS

RELATED PATENT DOCUMENTS

This patent document is the national stage filing under 35 U.S.C. §371 of International Application No. PCT/US2009/039949 filed on Apr. 8, 2009, which claims the benefit, under 35 U.S.C. §119(e), of U.S. Provisional Patent Application Ser. No. 61/047,219 filed on Apr. 23, 2008 and entitled "Systems, Methods and Compositions for Optical Stimulation of Target Cells;" each of these patent documents is fully incorporated herein by reference.

INCORPORATION-BY-REFERENCE OF MATERIAL SUBMITTED ELECTRONICALLY

Incorporated by reference in its entirety is a computer-readable nucleotide/amino acid sequence listing submitted concurrently herewith, and identified as follows: One 8,345 Byte ASCII (Text) file named "STFD_212PCT_ST25.txt" created on Apr. 7, 2009.

OVERVIEW

The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the CNS, and makes neuromodulation a difficult therapeutic endeavor. This architecture of the brain poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neurons using electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread the electrical current and increase the unintended stimulation of additional cells.

Another method of stimulus uses photosensitive bio-molecular structures to stimulate target cells in response to light. For instance, light activated proteins or molecules can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions.

Aspects of the invention are directed to photosensitive bio-molecular structures and related methods. The present invention is exemplified in a number of implementations and applications, some of which are summarized below.

According to one example embodiment of the present invention, an implantable arrangement is implemented having a light-generation device for generating light. The arrangement also has a biological portion that modifies target cells for stimulation in response to light generated by the light-generation means in vivo.

According to another example embodiment of the present invention, target cells are stimulated using an implantable arrangement. The arrangement includes an electrical light-generation means for generating light and a biological portion. The biological portion has a photosensitive bio-molecular arrangement that responds to the generated light by stimulating target cells in vivo. Stimulation may be manifested as either up-regulation, or down-regulation of activity at the target.

According to another example embodiment of the present invention, an implantable device delivers gene transfer vector, such as a virus, which induces expression of photosensitive bio-molecular membrane proteins. The device has a light generator, responsive to (for example, charged by or triggered by) an external signal, to generate light and a biological arrangement that includes the photosensitive bio-molecular protein that responds to the generated light by interacting with target cells in vivo. In this manner, the electronic portions of the device may be used to optically stimulate target cells. Stimulation may be manifested as either up-regulation (e.g., increased neuronal firing activity), or down-regulation (e.g., neuronal hyperpolarization, or alternatively, chronic depolarization) of activity at the target.

According to another example embodiment of the present invention, a method is implemented for stimulating target cells using photosensitive proteins that bind with the target cells. The method includes a step of implanting the photosensitive proteins and a light generating device near the target cells. The light generating device is activated and the photosensitive protein stimulates the target cells in response to the generated light.

Applications include those associated with any population of electrically-excitable cells, including neurons, skeletal, cardiac, smooth muscle cells, and insulin-secreting pancreatic beta cells. Major diseases with altered excitation-effector coupling include heart failure, muscular dystrophies, diabetes, pain, cerebral palsy, paralysis, depression, and schizophrenia. Accordingly, the present invention has utility in the treatment of a wide spectrum of medical conditions, from Parkinson's disease and brain injuries to cardiac dysrhythmias, to diabetes, and muscle spasm.

According to other example embodiments of the present invention, methods for generating an excitation neuron-current flow involve, in a neuron, engineering a protein that responds to light by producing an excitation current to encourage depolarization of the neuron. In one such method, the protein is derived from *Volvox carteri*.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

DETAILED DESCRIPTION

The present invention is believed to be useful for facilitating practical applications of a variety of photosensitive biomolecular structures, and the invention has been found to be particularly suited for use in arrangements and methods dealing with cellular membrane voltage control and stimulation. While the present invention is not necessarily limited to such applications, various aspects of the invention may be appreciated through a discussion of various examples using this context.

Consistent with one example embodiment of the present invention, a light-responsive protein/molecule is engineered in a cell. The protein affects a flow of ions across the cell membrane in response to light. This change in ion flow creates a corresponding change in the electrical properties of the cells including, for example, the voltage and current flow across the cell membrane. In one instance, the protein functions in vivo using an endogenous cofactor to modify ion flow across the cell membrane. In another instance, the protein changes the voltage across the cell membrane so as to dissuade action potential firing in the cell. In yet another instance, the protein is capable of changing the electrical properties of the cell within several milliseconds of the light being introduced.

Consistent with a more specific example embodiment of the present invention, a protein, herein identified as VChR1, from *Volvox carteri* is used for temporally-precise optical control of neural activity. VChR1 allows for selective excitation of single action potentials including the generation of rapid spike trains and sustained blockade of spiking over many minutes. The action spectrum of VChR1 is strongly red-shifted relative to ChR2 but operates at similar light power, and functions in mammals without exogenous cofactors. In one instance, VChR1 can be co-expressed with and NpHR and/or ChR2 in the target cells. Likewise, VChR1, NpHR and ChR2 can be targeted to *C. elegans* muscle and cholinergic motoneurons to control locomotion bidirectionally. In this regard, VChR1, NpHR and ChR2 form an optogenetic system for multimodal, high-speed, genetically-targeted, all-optical interrogation of living neural circuits.

Embodiments of the present invention are directed to the VChR1 protein. Various embodiments are directed toward a plasmid that contains the DNA or nucleotide sequence that expresses the VChR1 protein. Yet other embodiments are directed toward an expression vector for expression of the VChR1 protein. A non-exclusive list of expression vectors includes bacterial, viral and plant plasmids. Another embodiment of the present invention is directed to heterologous cells that contain the VChR1 protein.

Figure 1:
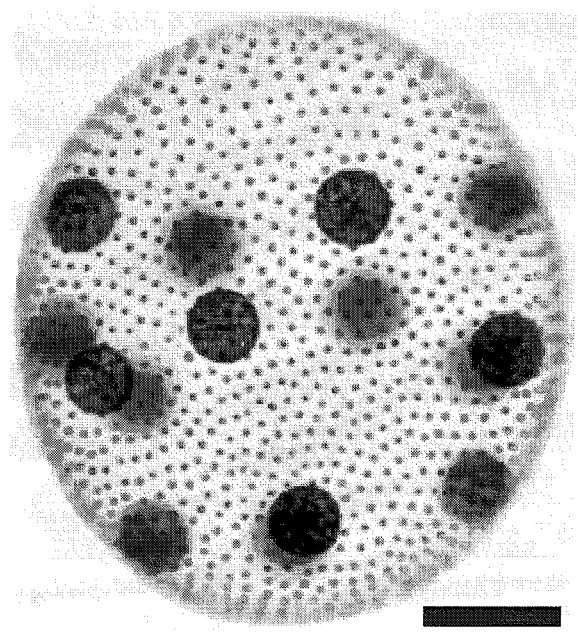
FIG. 1A shows a pheroidal alga *Volvox carteri*, consistent with an example embodiment of the present invention.
FIG. 1B shows all-trans retinal Schiff base and amino acid sequences of ChR2 (SEQ ID NO:1), ChR1 (SEQ ID NO:2), and VChR1 (SEQ ID NO:3), consistent with an example embodiment of the present invention.
FIG. 1C evoked photocurrents relative to light intensity, consistent with an example embodiment of the present invention.
FIG. 1D shows an inwardly rectifying current-voltage relationship, consistent with an example embodiment of the present invention.
FIG. 1E shows membrane currents relative to specific ions, consistent with an example embodiment of the present invention.
FIG. 1F shows activation percentage relative to optical wavelength, consistent with an example embodiment of the present invention.
Figure 1:
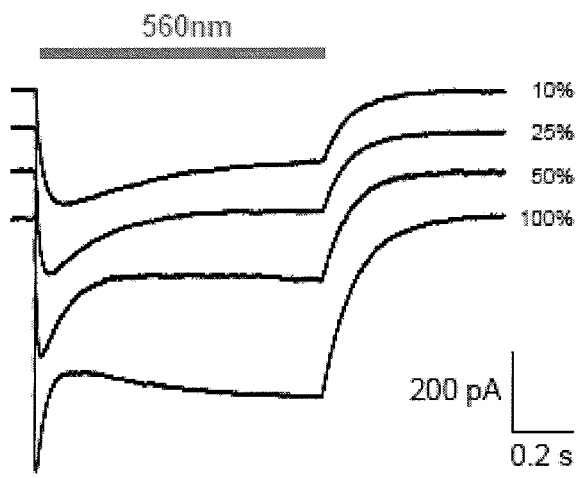
Figure 1:
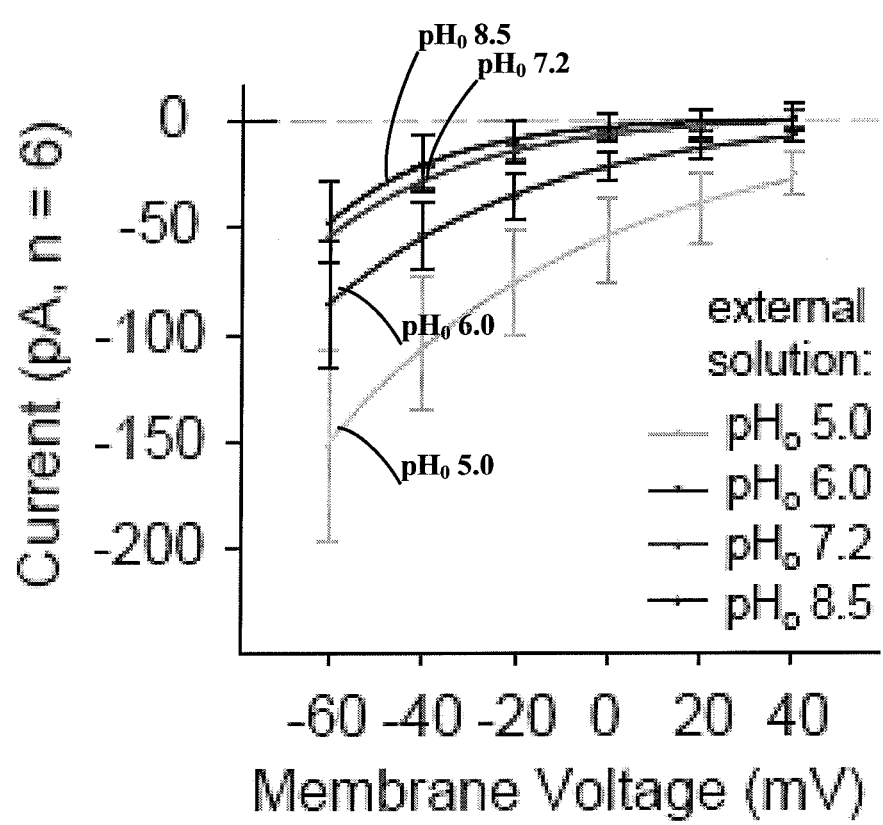
Figure 1:
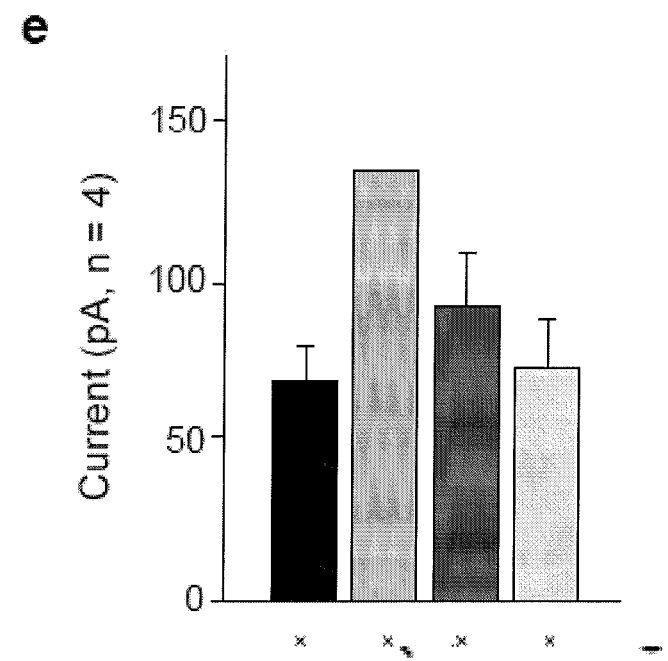
Figure 1:
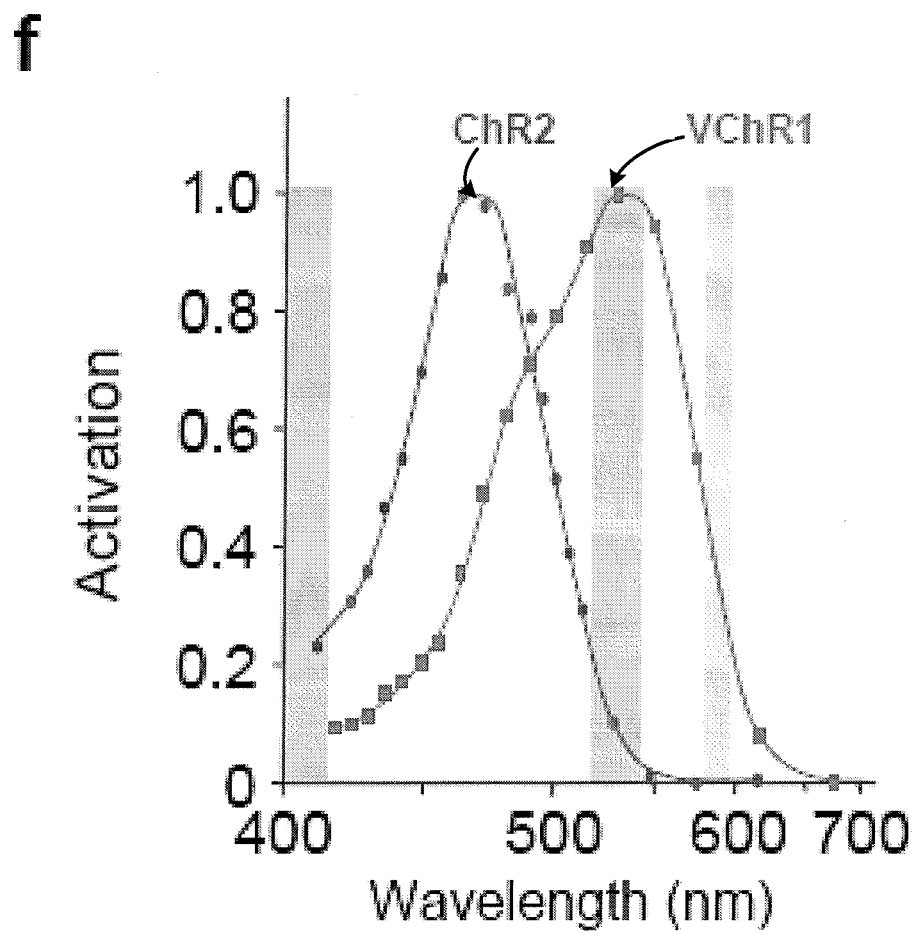

Aspects of the present invention are directed toward variations of the specific embodiment of VChR1 disclosed in FIG. 1B. One such aspect includes mutations of the protein. These mutations may, for example, target portions of the VChR1 protein that shift or otherwise change the wavelength of light that activates the protein.

Fast light-activated microbial proteins adapted for neuroscience, including the channelrhodopsin ChR2 and the halorhodopsin NpHR, permit millisecond-precision optical control of genetically-defined cell types within intact neural tissue. Since ChR2 is a blue light-driven cation channel that can activate neurons, and NpHR is a yellow light-driven chloride pump that can inhibit neurons, the combination of these two proteins allows independent neural excitation and inhibition in the same preparation. A third major optogenetic tool, namely a second cation channel with action spectrum significantly shifted relative to ChR2, would allow experimental testing of the differential contribution or interaction of two distinct cell types in circuit computation or behavior.

One ChR2-related sequence from the spheroidal alga *Volvox carteri* (FIG. 1A) has been described, but the absorption spectrum of the protein and the photocycle dynamics are virtually identical to those of ChR2. A second *Volvox* ChR more related to ChR1 from *Chlamydomonas reinhardtii* (FIG. 1B) was discovered. This new protein and variants thereof are herein referred to as VChR1.

In an experimental test, VChR1 was expressed in *Xenopus* oocytes and HEK293 cells, and found to evoke photocurrents were similar to those of ChR1 from *Chlamydomonas*. The photocurrents were graded with light intensity, and displayed inactivation from a fast peak toward a slightly reduced stationary plateau (FIG. 1C). The peak appeared preferentially at light of relatively high intensity, likely attributable to increased accumulation of an expected late non-conducting photocycle intermediate (FIG. 1C), and as light intensity approached saturation the evoked current displayed a characteristic minimum before steady-state is reached. VChR1 exhibited an inwardly rectifying current-voltage relationship (FIG. 1D) and under neuronal physiological conditions conducted chiefly Na+ but also H+, K+, and Ca2+ (FIG. 1E).

Primary-structural differences between VChR1 and the Chlamydomonas ChRs were identified to allow for prediction of the altered absorption properties (FIG. 1B, depicting SEQ. ID. NOs. 001 (ChR2), 002 (ChR1) and 003 (VChR1), with primary-structural differences highlighted). First, based on previous calculations of the electrostatic potential of bacteriorhodopsin (BR, absorption maximum at 570 nm) and sensory rhodopsin II (SRII, absorption maximum at 500 nm) and on additional quantum mechanical-molecular mechanical calculations (QM/MM), the counterion complex of the cofactor all-trans retinal Schiff base (RSB; FIG. 1B) will likely be most critical for color tuning, photoisomerization and photocycle dynamics. Based on homology with other microbial opsin genes for which the 3D structure is known, the counterion complex in ChR2 should be defined by R120, E123, and D253. However, these residues are fully conserved in both ChR1 and VChR1 (FIG. 1B, highlighted columns 104). Second, theoretical calculations in line with previous mutational experiments predict that three residues of the RSB binding pocket could significantly contribute to absorption differences among microbial rhodopsin proteins. These amino acids are G181, L182, and S256 in ChR2 (FIG. 1B sequence, highlighted columns 106); the former two are expected to be located near the RSB β-ionone ring (FIG. 1B structure, 108) and may, in conjunction with C183, determine absorbance spectrum, while S256 is instead likely adjacent to the protonated nitrogen of the RSB (FIG. 1G structure, 110). In VChR1 the β-ionone ring end of the RSB is expected to be more polar than in ChR1 and ChR2, since the two positions 181 and 183 have been substituted with a polar Ser, while conversely the RSB nitrogen environment is actually less polar with an Ala at position 256. The combination of these three exchanges at positions 181, 183, and 256 resulting in an expectation of a redistribution of positive charge along the RSB polyene system and a substantial redshift, likely by more than 40 nm, in VChR1 compared to ChR2.

Three other amino acids H114, E235, and E245 (FIG. 1B, highlighted columns 102) are expected to modulate the RSB charge distribution by long-range coupling, and here the H114N exchange in both VChR1 and ChR1 is further predicted to increase the RSB potential at the β-ionone end. The 495 nm absorbance maximum of ChR1 (which does not express well in neurons), is indeed slightly red-shifted from that of ChR2, but the combination of many significant changes in VChR1 predicted a robust wavelength shift on a scale useful for defining a new class of tool for neuroscience.

Figure 2:
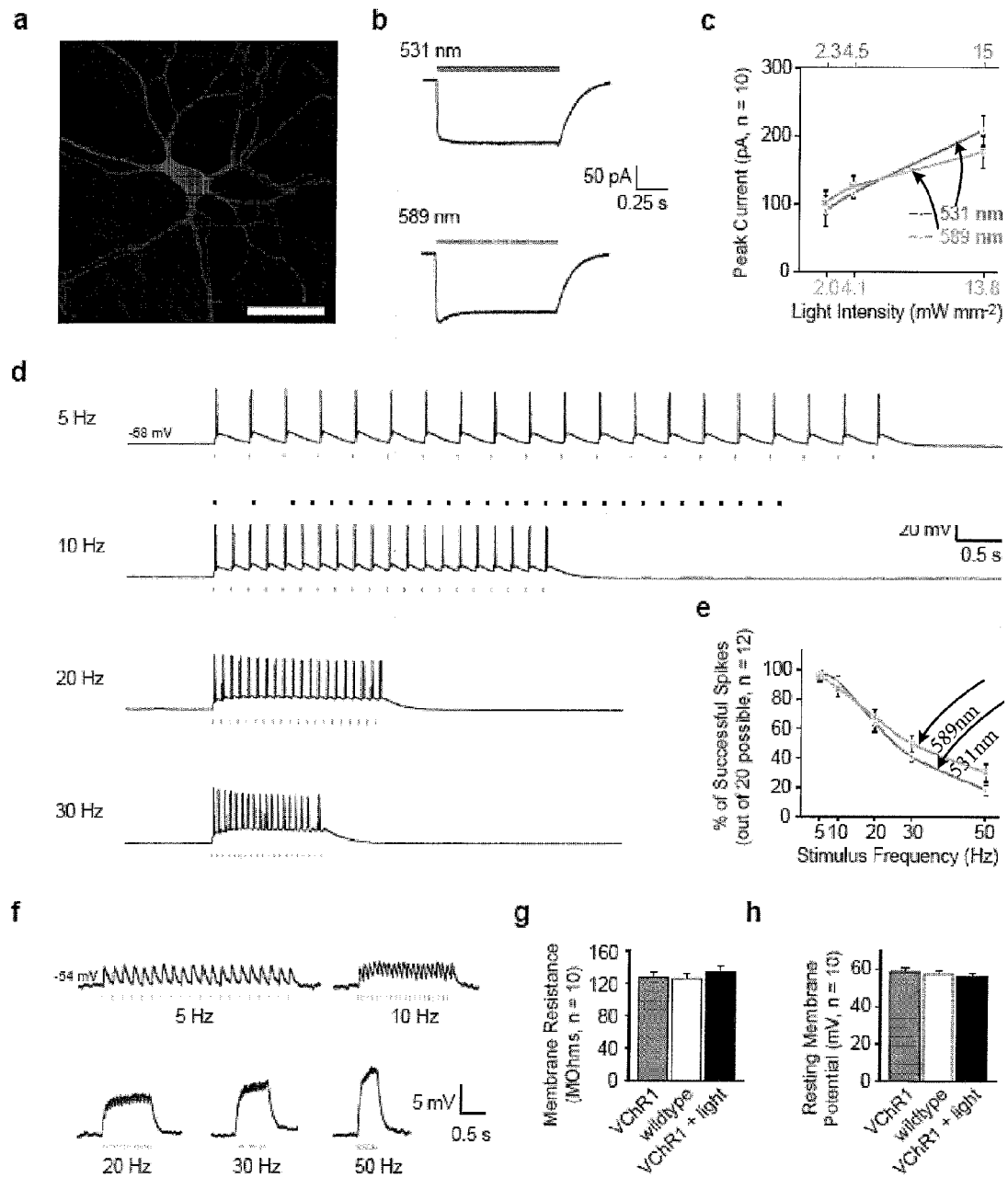
FIG. 2A shows neurons expressing VChR1-EYFP and exhibiting membrane-localized EYFP fluorescence, consistent with an example embodiment of the present invention.
FIG. 2B shows VChR1-EYFP neurons photocurrents when illuminated with 531 nm and 589 nm light, consistent with an example embodiment of the present invention.
FIG. 2C shows whole-cell inward currents for 531 nm and 589 nm light, consistent with an example embodiment of the present invention.
FIG. 2D shows twenty 5 ms light pulses delivered to VChR1-EYFP neurons in current clamp at various frequencies, consistent with an example embodiment of the present invention.
FIG. 2E shows the percentages of successful spikes at various frequencies, consistent with an example embodiment of the present invention.
FIG. 2F shows that increasing frequencies of light pulses delivered increased steady-state depolarization, consistent with an example embodiment of the present invention.
FIG. 2G shows the membrane resistance, consistent with an example embodiment of the present invention.
FIG. 2H shows resting membrane potential, consistent with an example embodiment of the present invention.

To initially probe the wavelength-dependence, VChR1-expressing oocytes were excited using 10 ns laser flashes across a range of wavelengths, to allow delineation of a markedly red-shifted action spectrum that revealed a maximum at ~535 nm and a small shoulder at lower wavelengths consistent with a second isoform peaking at 505 nm (FIG. 1F). A lentivirus carrying the alpha-CaMKII promoter to drive strong protein expression was constructed to test the function of VChR1 in neurons. To visualize VChR1 expression, the seven transmembrane domains of VChR1 (residues 1-300, based on homology with the first 315 residues of ChR2) were in-frame fused to the amino-terminus of yellow fluorescent protein (VChR1-EYFP). Neurons expressing VChR1-EYFP exhibited clearly membrane-localized EYFP fluorescence similar to that reported previously for ChR2-EYFP (FIG. 2A), with expression level slightly weaker compared with ChR2-EYFP using the same lentiviral alpha-CaMKII expression vector. Nevertheless, VChR1-EYFP neurons exhibited strong photocurrents when illuminated with 531 nm and even 589 nm light (FIG. 2B). Mean whole-cell inward currents were 208.8±22.3 pA (mean±s.e.m. reported unless otherwise stated, n=20) and 177.6±24.7 pA (n=10) when illuminated with 15 mW/mm2 of 531 nm light and 13.8 mW/mm2 of 589 nm light at the sample, respectively (FIG. 2C). Apparent time constants for the rise of the photocurrent were faster when closer to the wavelength of maximum activation due to the shift in absorption coefficient, with corresponding values of $\tau 531\_on=2.8±0.3$ ms and $\tau 589\_on=8.0±0.7$ ms (n=11 for 531 nm and n=10 for 589 nm). The corresponding decay time constants were $\tau 531\_off=133.4±11.7$ ms (n=11) and $\tau 589\_off=135.7±9.8$ ms (n=10).

The frequency dependence of VChR1 in evoking spikes was explored using trains of twenty 5 ms light pulses at 531 nm or 589 nm delivered to VChR1-EYFP neurons in current clamp (exemplar traces from 589 nm excitation in FIG. 2D). At up to 10 Hz, more than 90% of tested cells fired 100% of the action potentials in the train at either wavelength, and at 20 Hz cells typically fired in response to ~65% of light pulses (FIG. 2E). In these strongly expressing cells, reliable spiking could be driven up to 30 Hz (FIG. 2D; pyramidal neurons in culture typically cannot follow 50 Hz or beyond in response to either current injection or ChR2 photostimulation), and at 531 nm, doublets of spikes were occasionally evoked for each light pulse, most likely due to the slower Toff decay constant of 133 ms compared to 12 ms for ChR210. As with ChR2, VChR1 could also trigger EPSP-like subthreshold depolarizations with lower stimulation light intensities. Delivery of light pulse barrages evoked typical summation of the subthreshold membrane voltage changes, with increasing frequencies of light pulses delivering increased steady-state depolarization (FIG. 2F).

To test for possible effects on membrane integrity, the membrane resistance and resting membrane potential were compared (FIGS. 2G and 2H) by whole-cell patch clamp, among 1) VChR1-EYFPexpressing, 2) non-transduced, and 3) VChR1-EYFP-expressing neurons first patch-clamped 24 hr after exposure to a typical light pulse protocol (1 s of 20 Hz, 5 ms light flashes, once per minute, for 10 minutes). All cells recorded exhibited comparable values, suggesting that VChR1-EYFP expression did not significantly alter membrane electrical properties. Subcellular distribution appeared similar to that of ChR2, with strong membrane localization, and VChR1 was well tolerated by these neurons. Moreover, as with ChR2 and NpHR, no all-trans retinal supplementation was needed with after VChR1 transduction in neurons; these genes all encode microbial opsins, which require incorporation of all-trans retinal to form the RSB and become functional rhodopsins, but vertebrate neurons consistently have been found to convert expressed opsins into functional proteins without supplementation of chemical cofactors.

Figure 3:
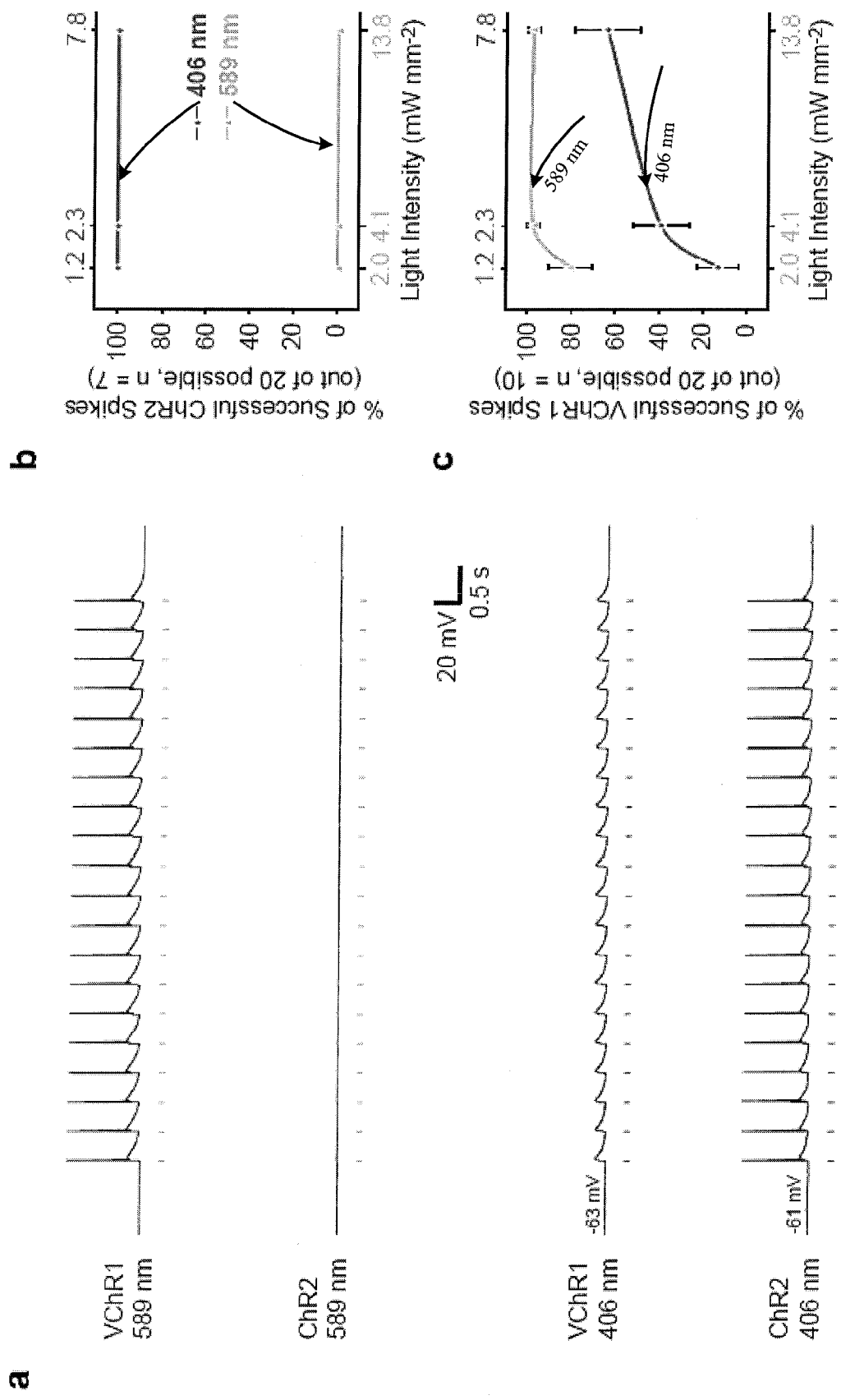
FIG. 3A shows voltage responses to optical stimulation at different wavelengths, consistent with an example embodiment of the present invention.
FIG. 3B shows a percentage of successful spikes for optical stimulation at different wavelengths and intensities, consistent with an example embodiment of the present invention.
FIG. 3C shows a percentage of successful spikes for optical stimulation at different wavelengths and intensities, consistent with an example embodiment of the present invention.

Testing was performed as to whether the pronounced spectral separation between ChR2 and VChR1 activation would be sufficient to enable separable activation using two different wavelengths of light. Based upon the action spectra (FIG. 1F), 406 nm and 589 nm were selected as likely optimal excitation wavelengths to probe separable activation of ChR2 and VChR1. For neurons expressing either ChR2 or VChR1, testing was performed for evoked action potentials in response to trains of twenty 5 ms light pulses (406 nm and 589 nm) delivered at 5 Hz. Each wavelength was tested at several different light intensities to determine parameters that maximize ChR2 activation while minimizing VChR1 activation at 406 nm, and vice versa. It was discovered that ChR2 and VChR1 neurons can be separately activated by 406 nm and 589 nm light respectively (FIG. 3A). In fact, no ChR2 neurons fired action potentials when illuminated with 589 nm light pulses since the absorption is practically zero at this wavelength, whereas VChR1 neurons fired reliably at this wavelength. Conversely all ChR2 neurons fired 20 action potentials when illuminated with 406 nm light, at all three light intensities (n=10, FIG. 3B). While VChR1 cells were capable of firing occasional action potentials in response to 406 nm flashes (generally, all rhodopsins exhibit some absorption at this wavelength due to transition to the second electronic state, S0->S2 transition), the percentage of spikes could be reduced to 13±9% when the 406 nm light intensity was reduced to 1.2 mW/mm2 (n=10, FIG. 3C), an intensity which continued to reliably and robustly drive spiking in the ChR2 neurons.

As currently implemented, the simultaneous application of VChR1 and ChR2 could be used to test progressive recruitment of different cell populations in controlling circuit behavior. For example, two different interneuron or neuromodulatory populations could be recruited in stepwise fashion: first by isolating population A with yellow light, followed by driving the combination of populations A and B with added blue light. This kind of experiment has been the primary driving force behind developing wavelength-shifted channelrhodopsins, as the complexity of neural information processing and interactions of different neuromodulatory systems will require fast optical excitation at more than one wavelength to test the importance of combinatorial computations and modulatory gating in neural circuit dynamics and behavior.

While the role of single cell types can be tested in separate experiments, for convenience in some experiments it might be useful to drive two isolated populations at different times. For this kind of experiment, an optimal strategy would entail use of the minimum 406 nm and 589 nm light intensities sufficient to separately trigger reliable ChR2 and VChR1 spikes respectively, which will simply require independent calibration in each experimental preparation (as in FIGS. 3A-C). A cross-taper of light colors can also be employed using a monochrometer or multiple filters; at yellow wavelengths, the VChR1-labeled population will be exclusively controlled, and as the excitation wavelength becomes progressively more blue beyond 535 nm, the contribution of the ChR2-labeled population will become steadily more dominant (FIG. 1F). Molecular refinements (e.g., blueshifting ChR2 and narrowing the spectrum of VChR1) can be implemented to provide further separation at the blue end of the spectrum.

The identification and characterization of VChR1 for yellow-light neural excitation here defines the third major functionally distinct category of fast optogenetic tools available for interrogating the organization and function of neural circuits, following the introduction of ChR2 for blue-light neural excitation and NpHR for yellow-light neural inhibition. In addition to its functionally significant red-shifted action spectrum, VChR1 displays additional properties that are of interest, including reduced ratio of peak to steady-state current (FIGS. 1C, 2B) compared with ChR2; while typically peak current magnitude in channelrhodopsins depends on light intensity, external pH, and membrane voltage, the steady-state to peak ratio is larger for VChR1 than ChR2 under all conditions we have explored.

The existence of two independently controllable excitation proteins opens the door for a variety of applications including, but not limited to, applications for treatment of a variety of disorders and the use of a plurality of light-responsive proteins that can be selected so as to respond to a plurality of respective optical wavelengths. The family of single-component proteins has been shown to respond to multiple wavelengths and intensities of light. Aspects of the invention allow for further mutations and/or searches for sequences that allow for additional optical wavelengths and/or individually controllable protein channels. Variations on the optical stimulus (e.g., a wavelength, intensity or duration profile) can also be used. For instance, stimulation profiles may exploit overlaps in the excitation wavelengths of two different ion channel proteins to allow excitation of both proteins at the same time. In one such instance, the proteins may have different levels of responsibility. Thus, in a neural application, one set of ion channels may produce spiking at a different success percentage relative to a second set of ion channels.

Many human applications of the present invention require governmental approval prior to their use. For instance, human use of gene therapy may require such approval. However, similar gene therapies in neurons (non-proliferative cells that are non-susceptible to neoplasms) are proceeding rapidly, with active, FDA-approved clinical trials already underway involving viral gene delivery to human brains. This is likely to facilitate the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging, for example cued-state PET or fMRI, may be used to locate a hyper metabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hyper metabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior. For further information in this regard, reference may be made to: Naqvi NH, Rudrauf D, Damasio H, Bechara A. "Damage to the insula disrupts addiction to cigarette smoking." Science. 2007 Jan. 26; 315(5811): 531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the $4^{th}$ and $5^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA31) provides stimulation, and hence neurotrophic drive to deteriorating areas. Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac disrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Growth of light-gated ion channels or pumps in the membrane of targeted thalamus neurons is effected. These modified neurons are then stimulated (e.g., via optics which may also gain access by the same passageway) by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R "Behavioral improvements with thalamic stimulation after severe traumatic brain injury," Nature, Vol. 448, Aug. 2, 2007, pp. 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyms (Cg25), yellow light may be applied with an implanted device. The goal would be to treat depression by suppressing target activity in manner analogous to what is taught by Mayberg H S et al., "Deep Brain Stimulation for Treatment-Resistant Depression," Neuron, Vol. 45, 651-660, Mar. 3, 2005, pp. 651-660, which is fully incorporated herein by reference. In an alternative embodiment, an optogenetic excitation stimulation method is to increase activity in that region in a manner analogous to what is taught by Schlaepfer et al., "Deep Brain stimulation to Reward Circuitry Alleviates Anhedonia in Refractory Major Depression," Neuropsychopharmacology 2007, pp. 1-10, which is fully incorporated herein by reference.

In yet another embodiment, the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate (e.g., 1 Hz or less) improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus. Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines. Disorders of intestinal hypermotility, including some forms of irritable bowel syndrome may be treated with optogenetic stabilization of neurons that control motility. Neurogentic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotic bodies") participate in the regulation of blood pressure and respiration by sending afferents via the vagus nerve (CNX), and other pathways to the medulla and pons, particularly the solitary tract and nucleus. Optogenetic excitation of the carotid bodies, aortic bodies, paraortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogenetic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Optogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus. In another embodiment, optogenetic stimulation to leptin-producing cells or to cells with leptin receptors within the hypothalamus may be used to decrease appetite and hence treat obesity.

Destructive lesions to the anterior capsule and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic pain can be treated using another embodiment of the present invention. Electrical stimulation methods include local peripheral nerve stimulation, local cranial nerve stimulation and "sub threshold" motor cortex stimulation. Reasonable autogenic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opiods may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optogenetic stabilization of the amygdale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) an cocaine-and-amphetamine-regulating transcript (CART), can be used to reduce compulsive sexual behavior. Optogenetic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogenetic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogetetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomaglovirus Immediate Early Enhancer), and other transcriptional or translational regulatory elements (e.g., Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassette to a specific region of interest. The choice of promoter will drive expression in a specific population of neurons. For example, using the CaMKIIa promoter will drive excitatory neuron specific expression of optogenetic probes. AAV will mediate long-term expression of the optogenetic probe for at least one year or more. To achieve more specificity, AAV may be pseudotyped with specific serotypes 1 to 8, with each having different trophism for different cell types. For instance, serotype 2 and 5 is known to have good neuron-specific trophism.

Another gene delivery mechanism is the use of a retrovirus. HIV or other lentivirus-based retroviral vectors may be used to deliver a promoter+optogenetic probe cassette to a specific region of interest. Retroviruses may also be pseudo-typed with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA-based viruses that can be used to deliver promoter+ optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfection of the local cells.

Various embodiments involve the use of various control elements. In addition to genetic control elements, other control elements (particularly promoters and enhancers whose activities are sensitive to chemical, magnetic stimulation or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Aspects of the present invention are directed towards testing a model of a neural circuit or disease. The model can define output response of the circuit as a function of input signals. The output response can be assessed using a number of different measurable characteristics. For instance, characteristics can include an electrical response of downstream neurons and/or behavioral response of a patient. To test the model, optogentic probes are expressed at an input position for the model. The optogenetic probes are stimulated and the output characteristics are monitored and compared to an output predicted by the model.

In certain implementations, the use of optogenetic probes allows for fine tuning of models defined using electrical probes. As electrical probes provide only limited ability to direct the stimulus and thus are not well suited for stimulus of certain areas without also directly stimulating nearby areas. Optogenetic probes disclosed herein provide a mechanism for more precise selection of the stimulus location. For instance, the stimulus from the optogenetic probes can be directed to very specific types of circuits/cells, such as afferent fibers. The following description provides an example implementation consistent with such an embodiment and is meant to show the feasibility and wide-ranging applicability for aspects of present invention.

According to one embodiment of the present invention, the invention may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

One such application involves long-term potentiation (LTP) and/or long-term depression (LTD) between two neural groups. By targeting the expression of VChR1 and ChR2 to different neural populations and stimulating each with a different frequency of light, LTP or LTD can be accomplished between the two groups. Each group can be individually controlled using the respective wavelength of light. This can be particularly useful for applications in which the spatial arrangement of the two groups presents issues with individual control using the same wavelength of light. Thus, the light delivery device(s) are less susceptible to exciting the wrong neural group and can be less reliant upon precise spatial location of the optical stimulus.

The delivery of the proteins to cells in vivo can be accomplished using a number of different deliver devices, methods and systems. On such delivery device is an implantable device that delivers a nucleotide sequence for modifying cells in vivo, such as a viral-vector. The implantable device can also include a light delivery mechanism. The light delivery can be accomplished using, for example, light-emitting diodes (LEDs), fiber optics and/or Lasers.

Another embodiment of the present invention involves the use of VChR1 in affecting stem cell fate including survival/death, differentiation and replication. The modulation of electrical properties has been shown to control stem cell fate. Various techniques can be used to provide stimulus patterns that modify stem cell fate. A specific example is consistent with those techniques used in Deisseroth, K. et al. "Excitation-neurogenesis coupling in adult neural stem/progenitor cells," Neuron 42, pp. 535-552 (2004), which is fully incorporated herein by reference. Another embodiment of the present invention is directed to the use of VChR1 to assess the efficacy of treatments. This can include, but is not limited to, drug screening, treatment regimens or modeling of treatments/disorders. In a specific embodiment, VChR1 is used as the primary optically responsive protein in such assessments. In alternate embodiments, VChR1 is used with other types of optically responsive proteins (e.g., ChR2 and/or NpHR) that respond to different wavelengths.

A specific embodiment of the present invention involves the use of VChR1 to generate a mammalian codon-optimized cDNA sequence and synthesized (DNA 2.0, Menlo Park, Calif.).

Lentiviral vector construction was accomplished using the following methods. VChR1-EYFP was constructed by fusing VChR1(1-300) with EYFP via a NotI restriction site. The fusion gene was then ligated into the AgeI and EcoRI sites of alpha-CaMKII lentiviral backbone to generate the pLenti-CaMKIIα-VChR1-EYFP-WPRE vector. Construction of the pLenti-CaMKIIa-ChR2-EYFP-WPRE vector was previously described. Recombinant lentiviruses were generated. For further details regarding the construction or use of such vectors reference can be made to Zhang, F., et al. "Multimodal fast optical interrogation of neural circuitry," Nature 446, pp. 633-639 (2007), which is fully incorporated herein by reference.

Cultured hippocampal neurons were prepared as described in Boyden, E. S., Zhang, F., Bamberg, E., Nagel, G. & Deisseroth, K. "Millisecond-timescale, genetically targeted optical control of neural activity," Nat Neurosci 8, pp. 1263-1268 (2005), which is fully incorporated herein by reference.

For whole-cell recording in cultured hippocampal neurons, the intracellular solution contained 129 mM K-Gluconate, 10 mM HEPES, 10 mM KCl, 4 mM MgATP, and 0.3 mM Na3GTP, titrated to pH 7.2. For cultured hippocampal neurons, Tyrode's solution was employed as the extracellular solution (125 mM NaCl, 2 mM KCl, 3 mM CaCl2, 1 mM MgCl2, 30 mM glucose, and 25 mM HEPES, titrated to pH 7.3). Recordings were conducted on an upright Leica DM-LFSA microscope equipped with a 40X water-immersion objective. Borosilicate glass (Sutter Instruments) pipette resistances were ~5 MΩ, with a range of 4-6 MΩ. Access resistance was 10-30 MΩ and monitored for stability throughout the recording. All recordings were conducted in the presence of synaptic transmission blockers as described in Boyden, E. S., Zhang, F., Bamberg, E., Nagel, G. & Deisseroth, K. "Millisecond-timescale, genetically targeted optical control of neural activity," Nat Neurosci 8, pp. 1263-1268 (2005).

For hippocampal neuron photostimulation, the following three filters were used in the Lambda DG-4 optical switch (Sutter Instruments) with a 300W Xenon lamp: 406 nm (FF01-406/15-25), 531 nm (FF01-531/22-25), and 589 nm (FF01-589/15-25) (Semrock).

For oocyte experiments, a synthetic DNA sequence corresponding to VChR11-313 (vchop1; adapted to human codon-usage, Geneart, Regensburg, Germany) was subcloned into VChR1 pGEMHE and pEGFP. cRNAs encoding ChR2 and VChR1, synthesized in vitro from pGEMHEplasmid by T7 RNA polymerase (mMessage mMachine, Ambion), were injected into the oocytes (50 ng/cell). The oocytes were stored for 3-7 days in the dark at 18° C. in Ringer solution (96 mM NaCl, 5 mM KCl, 1.8 mM CaCl2, 1 mM MgCl2, 5 mM MOPS-NaOH, pH 7.5) in the presence of 1 mg/ml penicillin, 1 mg/ml streptomycin, 1 μM all-trans-retinal, and 0.5 mM theophylline.

Two-electrode voltage clamp on *Xenopus laevis* oocytes were performed to obtain action spectra. 10 ns laser flashes (400-620 nm, 4-9×1019 photons s-1 m-2) from a Rainbow OPO (OPOTEK, Carlsbad, Calif.) pumped by the third harmonic of a Brilliant b Nd-YAG-Laser (Quantel, Les Ulis Cedex, France) were applied to the oocyte via a 1 mm light guide. The amplifier Tec-05X (NPI Electronic, Tamm, Germany) was compensated to keep the voltage change below 0.05 mV at a half saturating laser flash. Data acquisition and light triggering were controlled with pCLAMP software via DigiData 1440A interfaces (Molecular Devices, Sunnyvale, USA).

The following discussion includes a detailed discussion regarding results of an application for treatment and characterization of Parkinson's Disease (PD). This specific implementation and the corresponding results are not meant to be limiting.

To first address the most widely-held hypothesis in the field, we asked if direct, reversible, bona fide inhibition of local-circuit excitatory STN neurons would be therapeutic in PD. The STN measures <1 $mm^3$ in rats, but targeting accuracy can be aided by extracellular recordings during opsin vector introduction, since STN is characterized by a particular firing pattern which is distinguishable from bordering regions (FIG. 4A, FIG. 10C).

The STN is a predominantly excitatory structure embedded within an inhibitory network. This anatomical arrangement enables a targeting strategy for selective STN inhibition (FIG. 4B), in which eNpHR is expressed under control of the CaMKIIα promoter, selective for excitatory glutamatergic neurons and not inhibitory cells, fibers of passage, glia, or neighboring structures. In this way true optical inhibition is targeted to the dominant local neuron type within STN.

Optical circuit interventions were tested in rats that had been made hemiparkinsonian by injection of 6-hydroxydopamine (6-OHDA) unilaterally into the right medial forebrain bundle (MFB). Loss of nigral dopaminergic cells following 6-OHDA administration was confirmed by decreased tyrosine hydroxylase levels unilaterally in the substantia nigra pars compacta (FIG. 10A). These hemiparkinsonian rodents have specific deficits in contralateral (left) limb use and display (rightward) rotations ipsilateral to the lesion, which increase in frequency when the subjects are given amphetamine to facilitate functional evaluation, and decrease in frequency upon treatment with dopamine agonists or following electrical DBS (FIG. 4D, right). This amphetamine-induced rotation test is widely used for identifying treatments in hemiparkinsonian rodents, which can be complemented with other behavioral assays such as locomotion, climbing, and head position bias. To directly inhibit the excitatory STN neurons, we delivered lentiviruses carrying eNpHR under the CaMKIIα promoter to the right STN of the hemiparkinsonian rats. CaMKIIα::eNpHR-EYFP expression was specific to excitatory neurons (as shown by CaMKIIα and glutamate expression; FIG. 4B, right; FIG. 11A), robust (95.73%±1.96 s.e.m infection rate assessed in n=220 CaMKIIα positive cells), and restricted to the STN (FIG. 4B, left and middle). To validate the resulting physiological effects of optical control, a hybrid optical stimulation/electrical recording device (optrode) was employed in isoflurane-anesthetized animals to confirm that eNpHR was functional in vivo, potently inhibiting (>80%) spiking of recorded neurons in the STN (FIG. 4C; FIG. S13A, B; FIG. 14A). This cell type-targeted inhibition was temporally precise and reversible, and extended across all frequency bands of neuronal firing (FIG. 4C, FIG. 16A).

Figure 4:
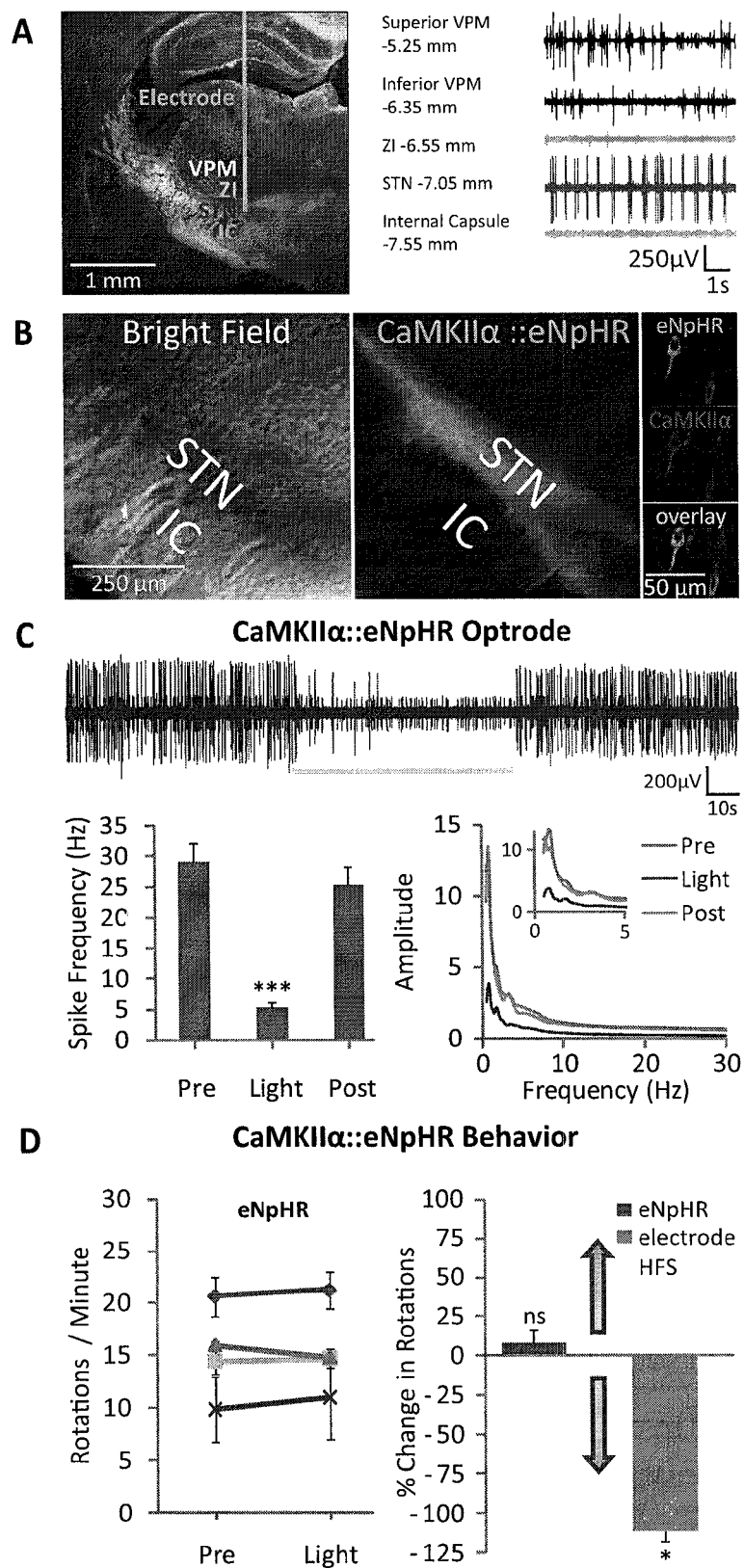
FIG. 4A-D shows direct optical inhibition of local subthalamic nucleus (STN) neurons.

For behavioral rotation assays in the hemiparkinsonian rats, the STN-targeted fiberoptic was coupled to a 561 nm laser diode to drive eNpHR. Electrical DBS was highly effective at reducing pathological rotational behavior, but despite precise targeting and robust physiological efficacy of eNpHR inhibition, the hemiparkinsonian animals did not show even minimal changes in rotational behavior with direct true optical inhibition of the local excitatory STN neurons (FIG. 4D). In addition, there was no effect on path length and head position bias in response to light during these experiments (see supplementary methods). While muscimol and lidocaine administration to the region of the STN in monkeys and rodents can relieve Parkinsonian symptoms (30), the data in FIG. 4 show that the more specific intervention of selectively decreasing activity in excitatory local neurons of the STN appeared not sufficient by itself to affect motor symptoms.

Another possibility is that DBS could be driving secretion of glial modulators which would have the capability to modulate local STN circuitry; this would be consistent with recent findings indicating that a glial-derived factor (adenosine) accumulates during DBS and plays a role in DBS-mediated attenuation of thalamic tremor. Indeed, the STN expresses receptors for glia-derived modulators which can inhibit postsynaptic currents in the STN. ChR2 presents an interesting possibility for recruitment of glia; when opened by light, in addition to $Na^+$ and $K^+$ ions, ChR2 can also pass trace $Ca^{2+}$ currents that trigger $Ca^{2+}$ waves in and activate ChR2-expressing astroglia. We employed a GFAP promoter to target ChR2 to local astroglia, validated with GFAP and S100β staining (FIG. 5A, FIG. 11B). Optrode recordings revealed that blue light stimulation of STN following transduction with GFAP::ChR2 reversibly inhibited neuronal firing in the STN (FIG. 5B, FIG. 12A), with variable delay on the timescale of seconds. However, recruiting astroglial cells by this mechanism was not sufficient to cause even trace responses in motor pathology in parkinsonian rodents (FIG. 5C, FIG. 12B). Path length and head position bias were also not affected by light during these experiments. While these data do not exclude the importance of local STN inhibition as a contributing factor in DBS response, as not all STN neurons may be affected in the same way by indirect glial modulation, the direct activation of local glial cells appeared not sufficient to treat parkinsonian symptoms, pointing to other circuit mechanisms.

Network oscillations at particular frequencies could play important roles in both PD pathology and treatment. For example, PD is characterized by pathological levels of beta oscillations in the basal ganglia, and synchronizing STN at gamma frequencies may ameliorate PD symptoms while beta frequencies may worsen symptoms. Because simple inhibition of excitatory cell bodies in the STN did not affect behavioral pathology, and since high-frequency stimulation (HFS: 90-130 Hz) is used for electrical DBS, we used ChR2 to drive high-frequency oscillations in this range within the STN. We injected CaMKIIα::ChR2 into the STN (FIG. 6A) and used pulsed illumination with a 473 nm laser diode to activate excitatory neurons in the STN (FIG. 6B, FIG. 14B) during behavioral testing in parkinsonian rodents (FIG. 6C, FIG. 12C). Despite robust effects on high-frequency power of neuronal spike rate in STN of anesthetized animals (FIG. 16B), HFS delivered locally to the STN area failed to affect PD behavioral symptoms (path length and head position bias were unchanged by light—see supplementary methods). Animals tested in parallel with beta frequency pulses also showed no behavioral response, indicating that (while not excluding a contributory role) directly generated oscillations within the STN excitatory neurons are not sufficient to account for therapeutic effects.

We have previously measured in cortical and hypothalamic tissue the propagation of blue light in the setting of laser diode-fiberoptic illumination; we observed that substantial tissue volumes (comparable to that of the STN) could reliably be recruited at a light power density sufficient to drive physiologically significant microbial opsin currents. It was important to repeat and extend these measurements to the PD setting. First, we confirmed that the propagation measurements of blue light (473 nm) in brain tissue represent a lower bound on the volume of tissue recruited, due to reduced scattering of lower-energy photons delivered from the 561 nm laser diode; therefore sufficient light power is present to activate opsins within 1.5 mm of the fiber for either wavelength of light (FIG. 7A). We next extended these findings with a functional assay for tissue recruitment under conditions mimicking our behavioral experiments (FIGS. 7B,C). After an in vivo optical stimulation paradigm targeted to the CaMKIIα::ChR2 expressing STN in freely moving rats, we performed immunohistochemistry for c-fos, a biochemical marker of neuronal activation. We observed robust c-fos activation in STN (FIG. 7B) over a widespread volume (FIG. 7C); indeed, as expected from our light scattering measurements and tissue geometry, we found that at least 0.7 $mm^3$ of STN is recruited by light stimulation, closely matching the actual volume of the STN (FIG. 7C). Therefore, light penetration was not limiting since the entire STN is recruited by the optical modulation paradigms of FIGS. 4-6.

Therapeutic effects could arise from driving axonal projections that enter the STN, as DBS electrodes will potently modulate not just local cells and their efferents, but also afferent fibers. Optogenetics discriminates these two possibilities, as the lentiviruses transduce somata without transducing afferent axons. To assess the possibility that PD motor behavioral responses are modulated by targeting afferent projections to the STN, we used Thy1::ChR2 transgenic mice in which ChR2 is expressed in projection neurons, and we verified that in Thy1::ChR2 line 18, ChR2-YFP is excluded from cell bodies in the STN but is abundant in afferent fibers (FIG. 8A).

We conducted optrode recordings in anesthetized 6-OHDA mice (FIG. 10B) to assess local effects on STN physiology of driving afferent axons selectively, and found frequency-dependent effects (FIG. 8B). First, we observed that HFS of afferent fibers to the STN potently reduced STN spiking across all frequency bands; this effect did not completely shut down local circuitry, as low-amplitude high-frequency oscillations persisted during stimulation (FIG. 8B; FIG. 13C, D; FIG. 14C). Next, we found that LFS of afferent fibers increased beta-frequency firing in the STN without affecting endogenous bursting (FIG. 8B, FIG. 14D). We next assessed the impact of these specific interventions on PD behavior in 6-OHDA mice, and for the first time among the optogenetic interventions, we observed marked effects. Driving STN afferent fibers with HFS robustly and reversibly ameliorated PD symptoms, measured by rotational behavior and head position bias (FIG. 8C). The HFS effects were not subtle; indeed, in nearly every case these severely parkinsonian animals were restored to behavior indistinguishable from normal, and in every case the therapeutic effect immediately and fully reversed, with return of ipsilateral rotations upon discontinuation of the light pulse paradigm Notably, treated animals could freely switch directions of movement and head position from left to right and vice versa. In striking contrast with optical HFS, optical LFS (20 Hz) of the same afferent fibers worsened PD symptoms by driving increased ipsilateral rotational behavior (FIG. 8C), demonstrating that behavioral effects seen do not result from simply driving unilateral activity. Therefore, in contrast to direct STN cellular interventions, driving STN afferent fibers with HFS and LFS differentially modulated PD symptoms in a manner corresponding to frequencies of stimulation linked clinically to ameliorated or exacerbated PD symptoms.

A diverse array of fibers from widespread brain areas converge on the STN, perhaps underlying the utility of the STN as a focal DBS target. Many of these afferents likely contribute together to the therapeutic effects, and it is unlikely that a single source of fibers completely accounts for the behavioral effects seen. However, we explored these afferents in greater detail to determine the general class of fibers that may be contributory.

Thy1::ChR2 animals display ChR2 expression chiefly in excitatory projection neurons. Indeed, the inhibitory markers GAD67 and GABA were not detectable in Thy1::ChR2 fibers within STN (FIG. 9A, left), effectively ruling out contributions from the GABAergic pallidal projections (LGP/GPe). We also found no localization of major neuromodulatory markers (dopamine and acetylcholine) within the STN Thy1::ChR2 fibers (FIG. 11C), ruling out dopaminergic SNr as a relevant fiber origin as well. We next explored possible sources of excitatory fibers, and found no expression of ChR2-YFP in the cell bodies of the excitatory parafascicular or pedunculopontine nuclei, potential contributors of excitatory fibers to the STN. Within neocortex of these mice, however, ChR2-YFP is expressed strongly in excitatory neurons that project to STN. Since pathologically strong connectivity between STN and primary motor cortex M1 has been suggested to underlie PD circuit dysfunction, we therefore explored M1 as a possible contributor.

Figure 15:
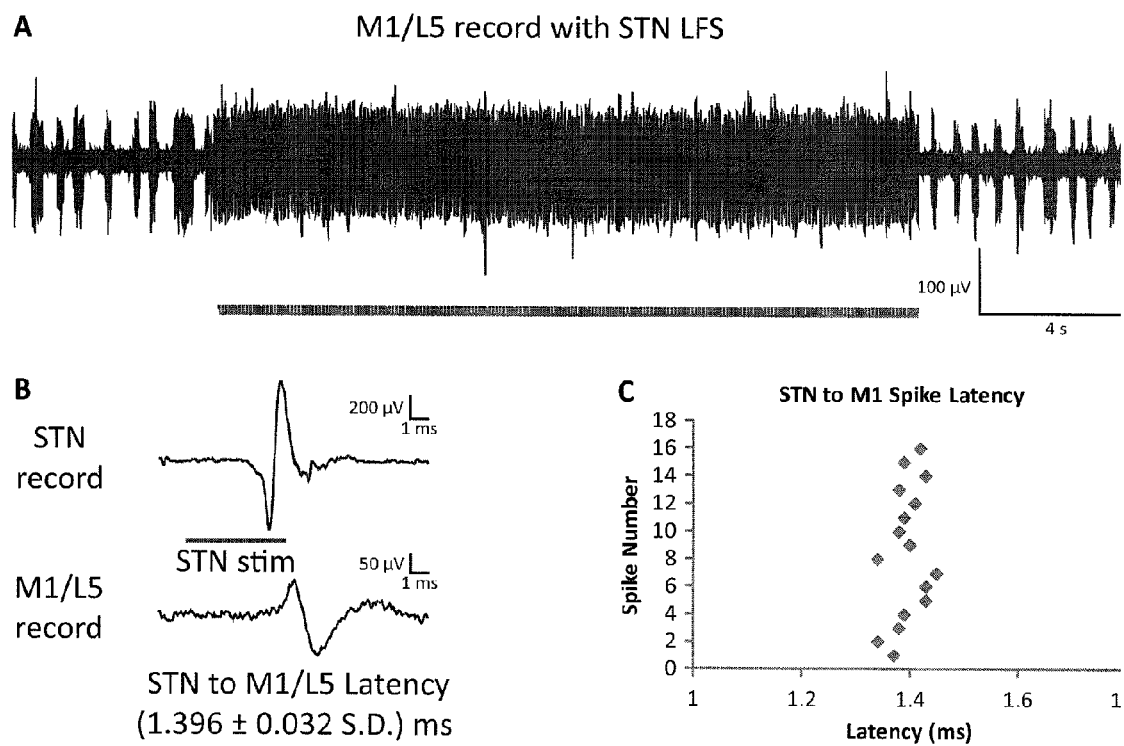
FIG. 15A-C shows latency of M1 response to optical stimulation of STN.

We verified in Thy1::ChR2 M1 the presence of strong and selective ChR2 expression largely restricted to layer V neurons and corresponding apical dendrites but not in cells within other layers (FIG. 9A, right). To probe the functional connectivity between these layer V projection neurons and STN in the PD animals, we conducted a separated-optrode experiment in anesthetized animals in which the fiberoptic and recording electrodes were placed in two different brain regions in Thy1::ChR2 animals (FIG. 9B). By driving M1 layer V projection neurons and simultaneously recording in both M1 and STN, we found that precise M1 stimulation of this kind potently influenced neural activity in the STN (FIG. 9C, FIGS. 16C, D), and that M1 Layer V neurons could be antidromically recruited by optical stimulation in the STN (FIG. 15). While as noted above, many local afferents in the STN region, including from the ZI, are likely to underlie the complex therapeutic effects of DBS, functional influences between M1 layer V and STN could be a significant contributor. Indeed, we found that selective M1 layer V HFS optical stimulation sufficed to ameliorate PD symptoms in a similar manner to STN stimulation in an array of measures ranging from rotational behavior (FIG. 9D) to head position bias and locomotion (FIGS. 9E, F). As with STN stimulation, pathological rotations and head position bias were reduced by optical HFS to M1; in contrast, while not augmenting the pathology, optical 20 Hz (LFS) stimulation to M1 had no therapeutic effect (FIGS. 9D, E, F), and even at the highest light intensities achievable without epileptogenesis, M1 LFS did not drive or modify rotational behavior, unlike M2 LFS cortical stimulation that can elicit contralateral rotations. Finally, increased functional mobility with M1 HFS but not LFS was confirmed with quantification of increased distance and speed of locomotion in PD Thy1::ChR2 mice; in the absence of amphetamine, M1 HFS allowed the otherwise bradykinetic animals to move freely without eliciting rotational behavior (FIG. 9F).

FIG. 4 shows direct optical inhibition of local STN neurons. (A) Cannula placement, virus injection, and fiber depth were guided by recordings of the STN, which is surrounded by the silent zona incerta (ZI) and internal capsule (IC). (B) Confocal images of STN neurons expressing CaMKIIα::eNpHR-EYFP and labeled for excitatory neuron-specific CaMKIIα (right). (C) Continuous 561 nm illumination of the STN expressing CaMKIIα::eNpHR-EYFP in anesthetized 6-OHDA rats reduced STN activity; representative optrode trace and amplitude spectrum shown. Mean spiking frequency was reduced from $29\pm3$ Hz to $5\pm1$ Hz (mean±s.e.m., $p<0.001$, Student's t-test, n=8 traces from different STN coordinates in 2 animals). (D) Amphetamine-induced rotations were not affected by stimulation of the STN in these animals ($p>0.05$, n=4 rats, t-test with $\mu=0$). The red arrow indicates direction of pathologic effects, while the green arrow indicates direction of therapeutic effects. The electrical control implanted with a stimulation electrode showed therapeutic effects with HFS (120-130 Hz, 60 μs pulse width, 130-200 μA, $p<0.05$, t-test with $\mu=0$). Percent change of −100% indicates that the rodent is fully corrected. Data in all figures are mean±s.e.m. ns $p>0.05$, *$p<0.05$, $p<0.01$, *$p<0.001$.

Figure 5:
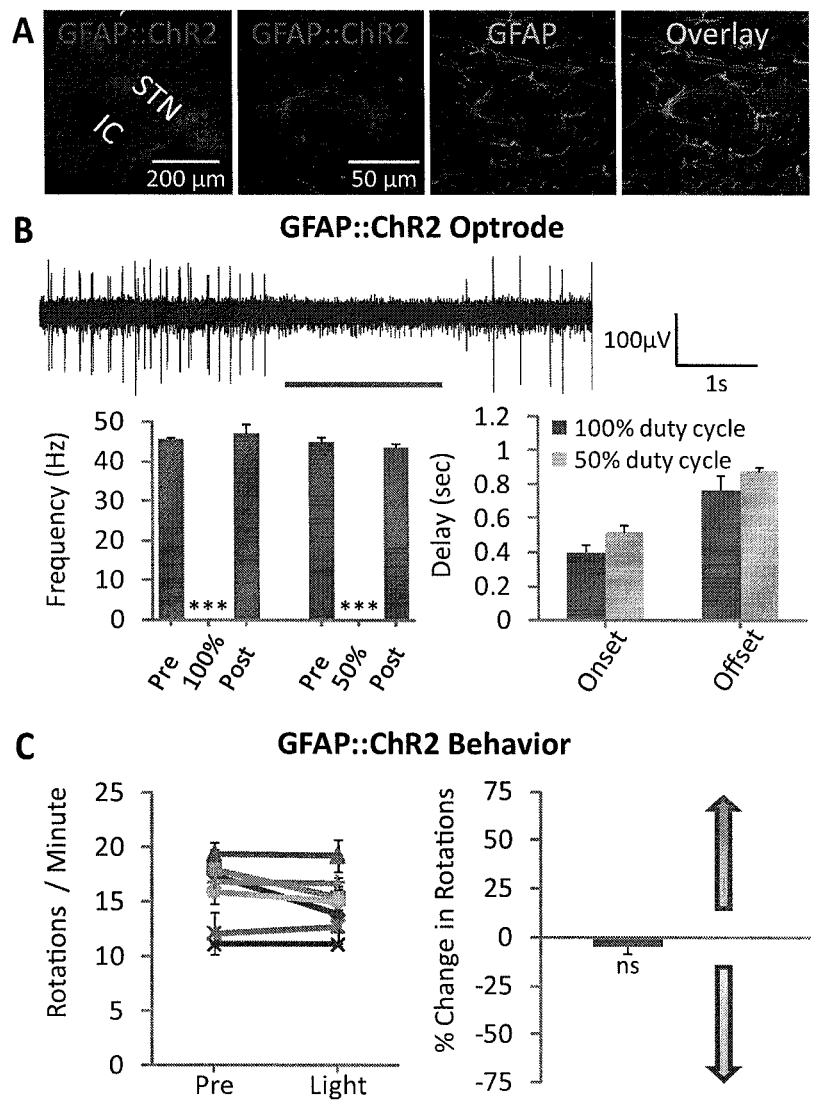
FIG. 5A-C shows targeting astroglia within the STN.

FIG. 5 shows targeting astroglia within the STN. (A) Confocal images show STN astrocytes expressing GFAP::ChR2-mCherry, costained with GFAP (right). (B) 473 nm illumination of the STN expressing GFAP::ChR2-mCherry in anesthetized 6-OHDA rats. Optrode recording revealed that continuous illumination inhibited STN activity with $404\pm39$ ms delay to onset and $770\pm82$ ms delay to offset (n=5 traces from different STN coordinates in 2 animals), while 50% duty cycle also inhibited spiking, with delay to onset of $520\pm40$ ms and delay to offset of $880\pm29$ ms (n=3 traces from different STN coordinates in 2 animals) with $p<0.001$. (C) Amphetamine-induced rotations were not affected by 50% duty cycle illumination in these animals (right, $p>0.05$, n=7 rats, t-test with $\mu=0$).

Figure 6:
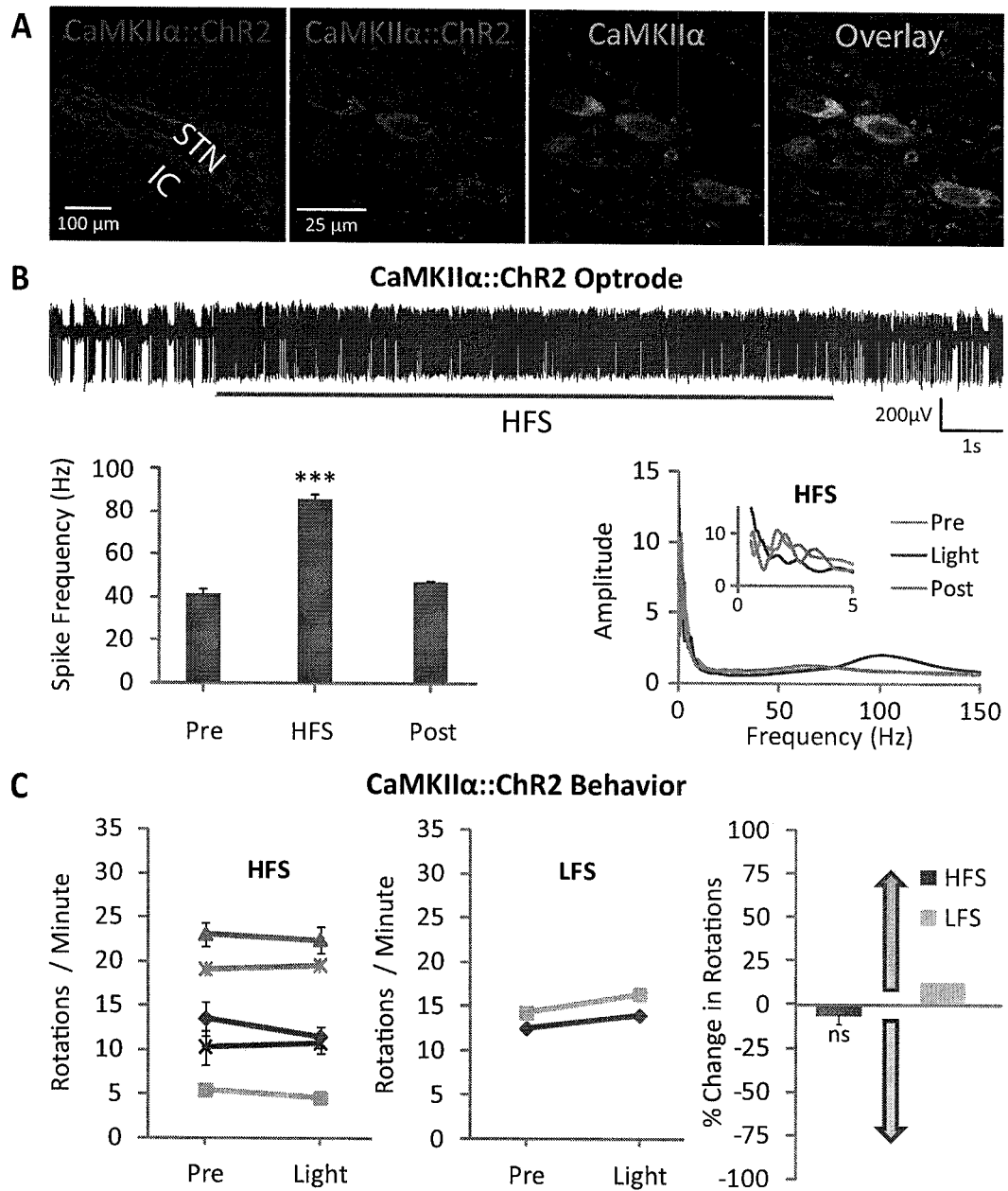
FIG. 6A-C shows optical depolarization of STN neurons at different frequencies.

FIG. 6 shows optical depolarization of STN neurons at different frequencies. (A) Confocal images of STN neurons expressing CaMKIIα::ChR2-mCherry and labeled for the excitatory neuron specific CaMKIIα marker. (B) Optical HFS (120 Hz, 5 ms pulse width) of the STN expressing CaMKIIα::ChR2-mCherry in 6-OHDA rats recorded with the optrode connected to a 473 nm laser diode (representative trace and amplitude spectrum shown). Frequency of spiking increased from $41\pm2$ Hz to $85\pm2$ Hz (HFS vs. pre, n=5 traces: $p<0.001$, t-test, post, n=3 traces; traces were sampled from different STN coordinates in 1 animal). (C) Amphetamine-induced rotations were not affected by high (left, 130 Hz, 5 ms, n=5 rats) or low (middle, 20 Hz, 5 ms, n=2 rats) frequency optical stimulation.

Figure 7:
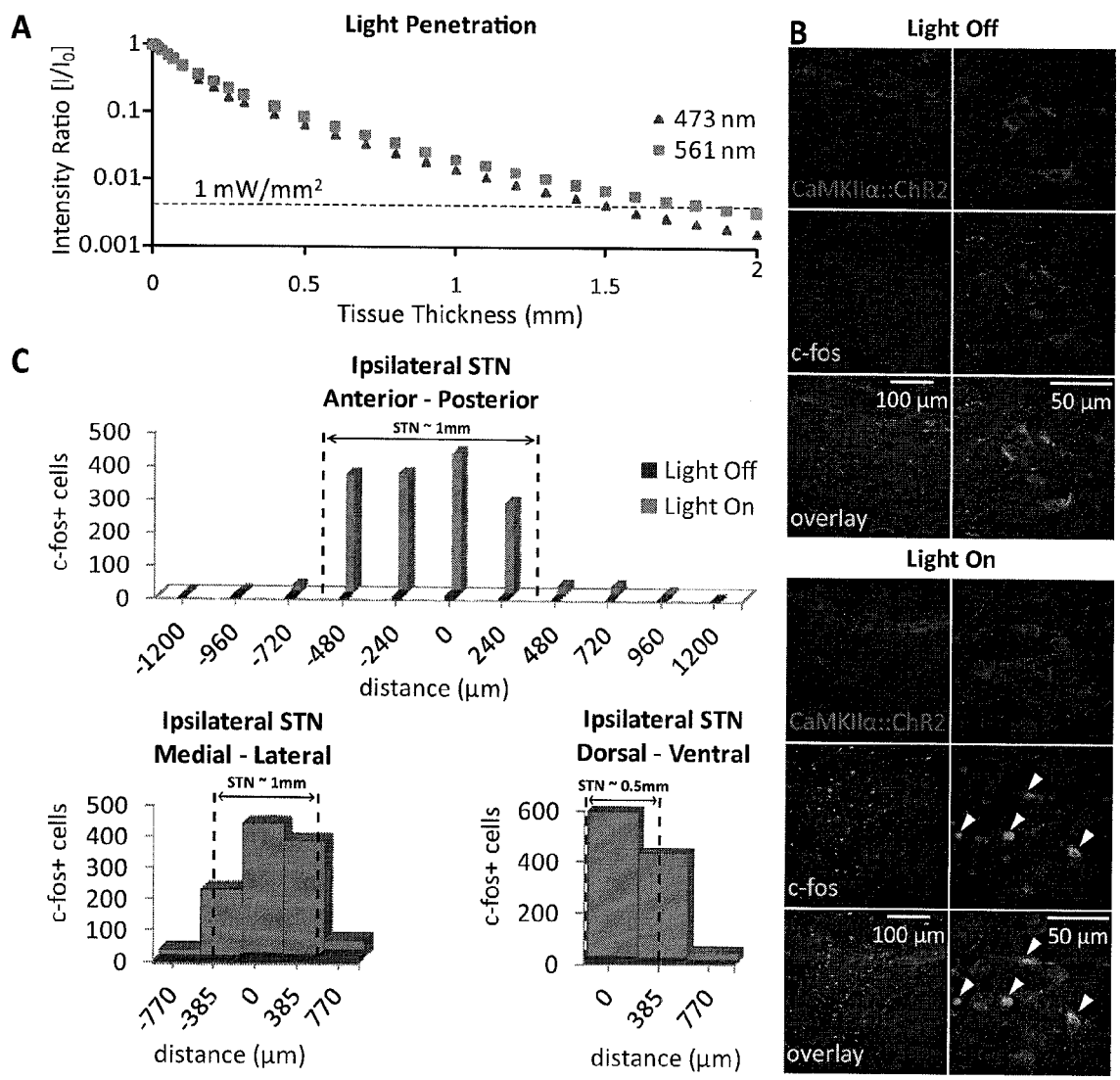
FIG. 7A-C shows quantification of the tissue volume recruited by optical intervention.

FIG. 7 shows quantification of the tissue volume recruited by optical intervention. (A) Intensity values for 473 nm (blue) and 561 nm (yellow) light are shown for a 400 μm fiber as a function of depth in brain tissue. The dashed line at 1 mW/mm$^2$ (30 mW light source) indicates the minimum intensity required to activate channelrhodopsins and halorhodopsins. (B) Confocal images of STN neurons expressing CaMKIIα::ChR2-mCherry and labeled for the immediate early gene product c-fos show robust neuronal activation produced by light stimulation in vivo. Arrowheads indicate c-fos positive cells. Freely moving rats expressing ChR2 in STN (same animals as in FIG. 6), were stimulated with 473 nm light (20 Hz, 5 ms pulse width). (C) The STN volume that showed strong c-fos activation was estimated to be at least 0.7 mm$^3$ (dashed lines indicate STN boundaries); robust c-fos activation was observed medial-lateral (1.155 mm), anterior-posterior (0.800 mm), and dorsal-ventral (0.770 mm) on subthalamic slices imaged by confocal microscopy with DAPI counterstain.

Figure 8:
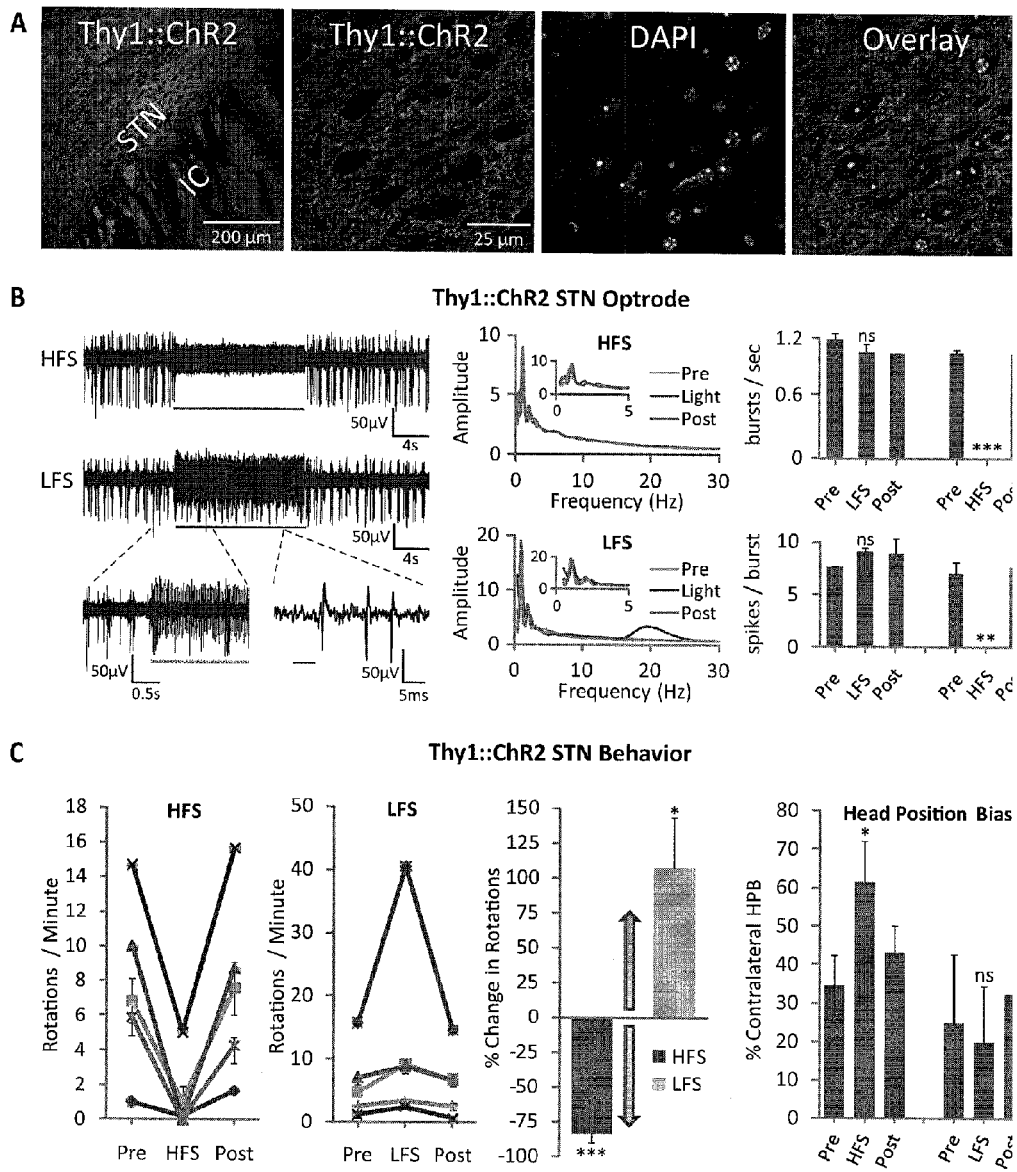
FIG. 8A-C shows selective optical control of afferent fibers in the STN.

FIG. 8 shows selective optical control of afferent fibers in the STN. (A) Confocal images of Thy1::ChR2-EYFP expression in the STN and DAPI staining for nuclei shows selective expression in fibers and not cell bodies (right). (B) Optical HFS (130 Hz, 5 ms pulse width) of the STN region in an anesthetized Thy1::ChR2-EYFP 6-OHDA mouse with 473 nm light inhibited STN large-amplitude spikes (sample trace, top left), while inducing smaller-amplitude high-frequency oscillations (FIGS. 13C, D; 14C). Optical LFS (20 Hz, 5 ms pulse width) produced reliable spiking at 20 Hz (bottom left). While HFS prevented bursting (top right, p<0.001, n=3), LFS had no significant effect on burst frequency by 2 sample t-test (p>0.05, n=3 traces) nor on spikes/burst (bottom right, p>0.05, n=3 traces). (C) Optical HFS to STN in these animals (left, 100-130 Hz, 5 ms, n=5 mice) produced robust therapeutic effects, reducing ipsilateral rotations and allowing animals to freely switch directions. In contrast, optical LFS (second left, 20 Hz, 5 ms, n=5 mice) exacerbated pathologic effects, causing increased ipsilateral rotations. Both effects were reversible (Post). Changes were significant by t-test with $\mu=0$ for both HFS (p<0.001, n=5 mice) and LFS (p<0.05, n=5 mice) compared to baseline (light off). (F) Contralateral head position bias also showed robust correction with HFS by 2 sample t-test (HFS vs. light off: p<0.05; n=2 mice), but not with LFS (LFS vs. light off: p>0.05, n=2 mice).

Figure 9:
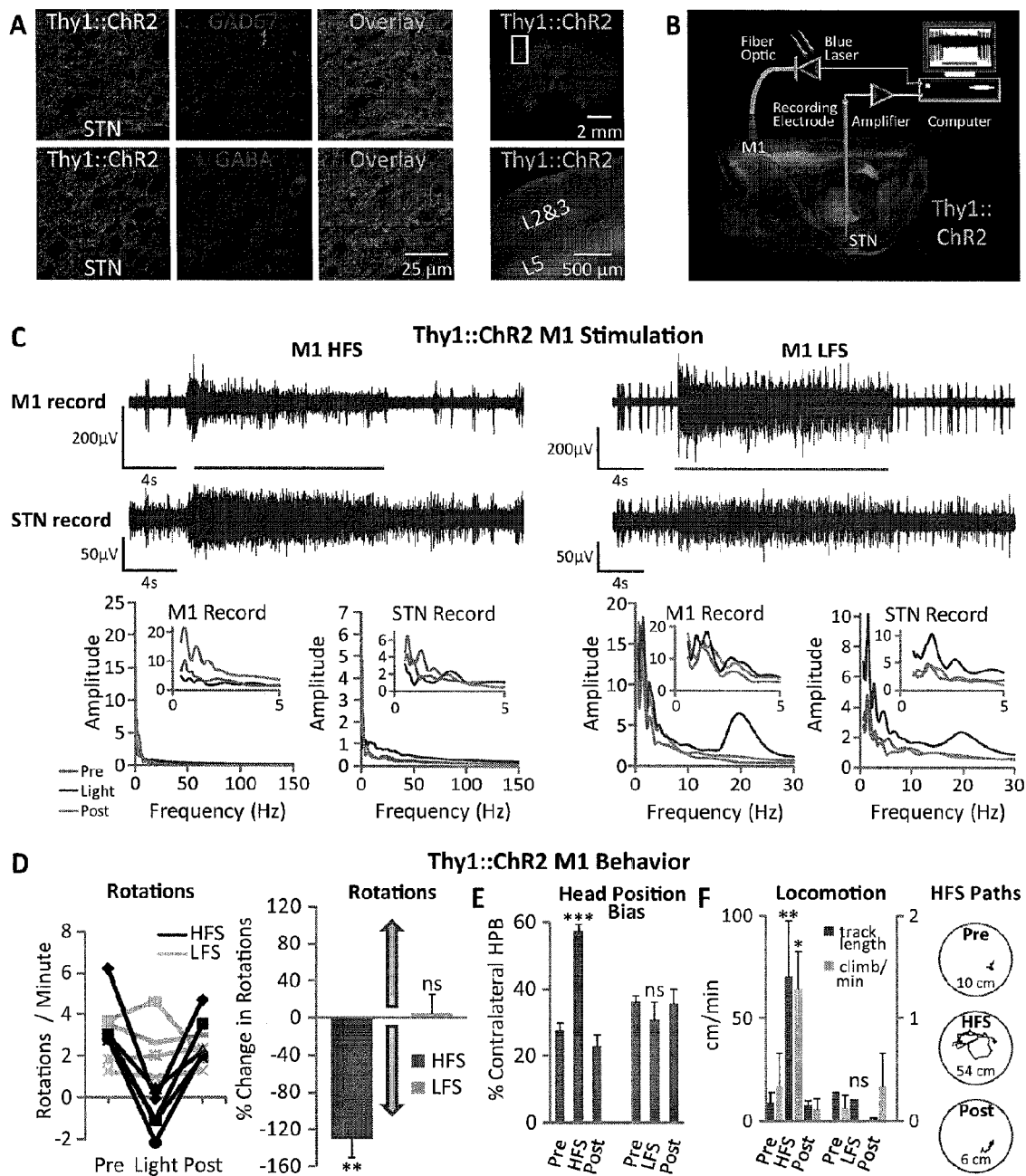
FIG. 9A-D shows selective optical stimulation of layer V neurons in anterior primary motor cortex.

FIG. 9 shows selective optical stimulation of layer V neurons in anterior primary motor cortex. (A) GAD67 and GABA staining showed no colocalization with Thy1::ChR2-EYFP in STN (left). Apical dendrites of layer V neurons can be seen rising to the pial surface (22, 23) (right). (B) Schematic for optical stimulation of M1 with simultaneous recording in STN of Thy1::ChR2 mice. (C) Optical stimulation (473 nm) of M1 and simultaneous recording in STN of anesthetized Thy1::ChR2 mice. Optical HFS (130 Hz, 5 ms pulse width) of M1 modulated activity in both M1 and STN. Optical LFS (20 Hz, 5 ms) of M1 produced 20 Hz tonic firing in both M1 and STN. (D) Optical HFS (130 Hz, 5 ms pulse width) reduced amphetamine-induced ipsilateral rotations in 6-OHDA Thy1::ChR2 mice (p<0.01, n=5 mice) in contrast to optical LFS (20 Hz, 5 ms pulse width, p>0.05, n=4 mice); t-test with $\mu=0$. (E) Contralateral head position bias was corrected in HFS (HFS vs. light off: p<0.001, n=4 mice), while LFS had little effect (LFS vs. light off: p>0.05, n=3 mice); 2-sample t-test. (F) HFS but not LFS to M1 significantly increased path length (HFS, p<0.01, n=2 mice) and climbing (p<0.05, n=3 mice); 2-sample t-test. Sample paths before, during, and after HFS are shown (100 seconds each, path lengths noted in cm).

According to a specific implementation, the following steps followed in obtaining the results discussed herein. To verify the phenotype of cells and measure c-fos activity, rodents were anaesthetized with 65 mg/kg sodium pentobarbital and transcardially perfused with ice-cold 4% paraformaldehyde (PFA) in PBS (pH 7.4). Brains were fixed overnight in 4% PFA and then equilibrated in 30% sucrose in PBS. 40 pun-thick coronal sections were cut on a freezing microtome and stored in cryoprotectant at 4° C. until processed for immunohistochemistry. Free-floating sections were washed in PBS and then incubated for 30 min in 0.3% Triton X-100 (Tx100) and 3% normal donkey serum (NDS). Slices were incubated overnight with primary antibody in 0.01% Tx100 and 3% NDS (rabbit anti-cfos 1:500, rabbit anti-GFAP 1:500, mouse anti-MAP2 1:500, mouse anti-GAD67 1:500, rabbit anti-GABA 1:200, mouse anti-vGlut1 1:500, mouse anti-vGlut2 1:500, mouse anti-CaMKIIα 1:200, mouse anti-S100 β 1:250, rabbit anti-glutamate 1:200, chicken anti-tyrosine hydroxylase 1:500, and goat anti-choline acetyltransferase 1:200). Sections were then washed and incubated with secondary antibodies (1:1000) conjugated to FITC, Cy3 or Cy5 for 3 hrs at room temperature. Following a 20 min incubation with DAPI (1:50,000) sections were washed and mounted on microscope slides with PVA-DABCO.

Confocal fluorescence images were acquired on a scanning laser microscope using a 20×/0.70NA or a 40×/1.25NA oil immersion objective. To determine the volume of c-fos activation, serial stack images covering a depth of 20 µm through multiple medial-lateral, anterior-posterior and dorsal-ventral subthalamic sections were acquired using equivalent settings. The image analysis software calculated the number of c-fos positive cells per field by thresholding c-fos immunoreactivity above background levels and using the DAPI staining to delineate nuclei. To determine the rate of viral transduction we determined the percentage of CaMKIIα-immunoreactive neurons per 40× field that were also eNpHR-YFP positive in multiple serial stack images of subthalamic sections. Large field images of entire slices were collected on a Leica MZ16FA stereomicroscope.

Lentiviral vectors carrying the genes used were constructed using cloning techniques. The CaMKIIα::eNpHR construct was produced by PCR amplification of the eNpHR-EYFP construct previously published and cloned in-frame into the AgeI and EcoRI restriction sites of a lentivirus carrying the CaMKIIα promoter. The CaMKIIα::ChR2 construct was produced by PCR amplification of the ChR2-mCherry construct and was also cloned in-frame into the AgeI and EcoRI restriction sites of a lentivirus carrying the CaMKIIα promoter. The GFAP::ChR2 construct was produced by replacing the CaMKIIα promoter with the GFAP promoter in the CaMKIIα::ChR2-mCherry construct using the AgeI and PacI restriction enzyme sites.

High titer lentivirus (>$10^9$ pfu/mL) was then produced via calcium phosphate co-transfection of 293FT cells with the lentiviral vector, pCMVΔR8.74 and pMD2.G (S2). 24 h post-transfection, 293FT cells were switched to serum-free medium containing 5 mM sodium butyrate; the supernatant was collected 16 h later and concentrated by ultracentrifugation at 50,000×g with 20% sucrose cushion. The resulting viral pellet was resuspended in phosphate buffered saline at $\frac{1}{1000}$th of the original volume.

To ensure that there would be no significant expression leak in non-targeted cell types, we employed a Cre-inducible AAV vector with a double-floxed inverted open reading frame (ORF), wherein the ChR2-EYFP sequence is present in the antisense orientation. Upon transduction, Cre-expressing cells invert the ChR2-EYFP ORF in a stable, irreversible fashion and thereby activate sustained ChR2-EYFP expression under control of the strong and constitutively active elongation factor 1α (EF-1α) promoter (Feng Zhang, unpublished results). To construct Cre-activated recombinant AAV vectors, the DNA cassette carrying two pairs of incompatible lox sites (loxP and lox2722) was synthesized and the ChR2-EYFP transgene was inserted between the loxP and lox2722 sites in the reverse orientation. The resulting double-foxed reverse ChR2-EYFP cassette was cloned into a modified version of the pAAV2-MCS vector carrying the EF-1α promoter and the Woodchuck hepatitis virus posttranscriptional regulatory element (WPRE) to enhance expression. The recombinant AAV vectors were serotyped with AAV5 coat proteins and packaged by the viral vector core at the University of North Carolina. The final viral concentration was $2 \times 10^{12}$ genome copies (gc)/mL.

Adult rats (female Fisher, 200-300 g) and mice (male and female, C57BL/6 background, 15-30 g) were the subjects of these experiments. Animal husbandry and all aspects of experimental manipulation of our animals were in strict accord with guidelines from the National Institute of Health and have been approved by members of the Stanford Institutional Animal Care and Use Committee. All surgeries were performed under aseptic conditions. Rodents were anaesthetized using 1.5% isoflurane (for surgeries longer than 1 hr) or i.p. injection (90 mg/kg ketamine and 5 mg/kg xylazine for rats; 80 mg/kg and 15-20 mg/kg, respectively, for mice). The top of the animal's head was shaved, cleaned with 70% ethanol and betadine and then placed in a stereotactic apparatus. Ophthalmic ointment was applied to prevent eye drying. A midline scalp incision was made and then small craniotomies were performed using a drill mounted on the stereotactic apparatus for the 6-OHDA injection in the medial forebrain bundle (rat: −2 AP, 2 ML, −7.5 DV; mouse: −1.2 AP; 1.2 ML, −4.75 DV) and virus injection in the STN (rat: −3.6 mm AP, 2.5 mm ML; mouse: −1.9 mm AP, 1.7 mm ML).

For rodents that were injected with lentivirus in the STN, in vivo extracellular recording was used to accurately determine the location of the STN along the dorsal-ventral axis. The depth was around −7 mm in rats and −4 mm in mice. The concentrated lentivirus (described above) was delivered to the STN using a 10 μl syringe and a thin 34 gauge metal needle; the injection volume and flow rate (3 sites within the STN along the dorsal-ventral axis; each injection was 0.6 μl at 0.1 μl/min) was controlled with an injection pump. After the final injection, the needle was left in place for 10 additional minutes and then slowly withdrawn.

6-OHDA was then used to lesion the substantia nigra and produce hemi-Parkinsonian rodents. Desipramine (20 mg/kg for rats; 10 mg/kg for mice; noradrenergic reuptake inhibitor to prevent damage to noradrenergic terminals) was administered, followed ~30 minutes later by 6-OHDA (8 μg/4 μl for rats; 6 μg/2 μl for mice) with 0.1% ascorbic acid (to prevent degradation of 6-OHDA) into the right medial forebrain bundle (rat: −2 AP, +2 ML, and −7.5 DV; mouse: −1.2 AP, +1.2 ML, and −4.75 DV). The perfusion for the 6-OHDA injection (rat: 4 μl, mouse 2 μl) was at the rate of 1.2 μl/min for 4 min, and the needle was left in situ for an additional 5 minutes.

A fiber guide (rat: C312G, mouse: C313G) was beveled to form a sharp edge (to more easily penetrate brain tissue and reduce tissue movement), and then inserted through the craniotomy to a depth of approximately 400 μm above the STN or the anterior primary motor cortex (mouse: 2 AP, 2 ML, 0.5 DV). One layer of adhesive cement followed by cranioplastic cement was used to secure the fiber guide system to the skull. After 20 min, the scalp was sealed back using tissue adhesive. The animal was kept on a heating pad until it recovered from anesthesia. Buprenorphine (0.03 mg/kg) was given subcutaneously following the surgical procedure to minimize discomfort. A dummy cannula (rat: C312G, mouse: C313G) was inserted to keep the fiber guide patent.

For electrical DBS control rodents, a stimulation electrode (MS303/3-B) was implanted in the STN. The procedure above was followed for OHDA injection, in vivo extracellular recording was then used to determine the depth of the STN, and the stimulation electrode was inserted to that depth and secured using one layer of adhesive cement followed by cranioplastic cement. Tissue adhesive was used to reseal the scalp, the animal was kept on a heating pad until recovery from anesthesia and buprenorphine was given to minimize discomfort. A dust cap (303DC/1) was then used to cover the electrode contacts.

Simultaneous optical stimulation and electrical recording in a single region in living rodents was done as described previously using an optrode composed of an extracellular tungsten electrode (1 MΩ, ~125 μm) tightly attached to an optical fiber (~200 μm) with the tip of the electrode deeper (~0.4 mm) than the tip of the fiber, to ensure illumination of the recorded neurons. For stimulation and recording in two distinct regions, small craniotomies were created above both target regions, and a fiber or optrode was placed above one region through one craniotomy and a plain electrode or optrode was placed in the other region through a separate craniotomy (see FIG. 9B for diagram). Stimulation in the anterior motor cortex was achieved by placing the optical fiber just above the brain surface, activating layer 5 of the cortex; for STN stimulation, the fiber was 300 μm above the STN. The STN was identified using its highly stereotyped firing pattern and the fact that it is surrounded dorso-ventrally by silent regions. The optical fiber was coupled to a 473 nm or 561 nm laser diode (30 mW fiber output) from CrystaLaser. Single unit recordings were done in rats anesthetized with 1.5% isoflurane and mice anesthetized with intraperitoneal injections of ketamine (80 mg/kg)/xylazine (15-20 mg/kg) cocktail. pClamp 10 and a Digidata 1322A board were used to both collect data and generate light pulses through the fiber. The recorded signal was band pass filtered at 300 Hz low/5 kHz high (1800 Microelectrode AC Amplifier). For precise placement of the fiber/electrode pair, stereotactic instrumentation was used.

For behavior, multimode optical fibers (NA 0.37; rat: 400 μm core, BFL37-400; mouse: 300 μm core, BFL37-300) were precisely cut to the optimal length for maximizing the volume of the STN receiving light. About one week before behavior, an extracellular recording electrode was used to determine the depth of the dorsal border of the STN from the tip of the cannula guide and fibers were cut to be 200-300 μm shorter. For anterior motor cortex stimulation, the fiber was placed above layer 5 (less than a millimeter deep). To ensure stability of the fiber during testing in moving animals, an internal cannula adapter was glued to the stripped optical fiber. To insert the fiber, rodents were briefly placed under isoflurane and the fiber was inserted while the animal was recovering from anesthesia. The internal cannula adapter snapped onto the cannula guide and the bottom half of the plastic portion of a dummy cannula was also used to ensure the adapter remained connected to the top of the cannula guide.

For optical stimulation, the fiber was connected to a 473 nm or 561 nm laser diode (20 mW fiber output) through an FC/PC adapter. Laser output was controlled using a function generator (33220A) to vary the frequency, duty cycle, and intensity. For Thy1::ChR2 animals, the average minimum intensity used to produce therapeutic behavior was 10 mW. A custom aluminum rotating optical commutator was used to release torsion in the fiber caused by the animal's rotation.

Motor behavior was assessed using amphetamine-induced rotations, head position bias, climbing, and track length. Animals were accepted for experimental investigation only if amphetamine reliably induced rotations in the ipsilateral direction confirming a 6-OHDA lesion of the substantia nigra. Before and after each stimulation trial, a trial of equal length with the light off was used as a control. Each of these trials was about 3 minutes long making the entire off-on-off sequence 9 minutes long. For amphetamine-induced behavior, amphetamine (rat: 2 mg/kg; mouse: 2.6 mg/kg) was injected 30 minutes before behavioral measurements; the fiber was inserted into the cannula and the rodent placed in an opaque, non-reflective cylinder (rat: diameter 25 cm, height 61 cm; mouse: diameter 20 cm, height 46 cm) 10 minutes before the behavioral experiments. Rotations ipsilateral to the 6-OHDA lesions (clockwise turns) were counted, and contralateral rotations were subtracted. The percentage change calculation considered the change in rotational bias relative to the period without stimulation. Head position bias was determined by counting the number of head tilts (>10° deviation left or right of midline) over time. Each time the rodent rose up and touched either paw to the wall of the cylinder was counted as an instance of climbing. Track length was measured with Viewer. After the completion of behavior experiments, cannula placement was confirmed by slicing.

For experiments where optical stimulation did not produce a change in the rodent behavior, we also collected path length and head position bias data while the rodents were under amphetamine. Continuous 561 nm illumination of the STN expressing CaMKIIα::eNpHR-EYFP in 6-OHDA rats did not affect path length (cm/min; light on vs. light off: 757.05±163.11 vs. 785.74±157.56, p=0.90, n=4 rats; mean±s.e.m; 2-sample t-test) or head position bias (% of time to the right; light on vs. light off: 99.92±0.08 vs. 99.75±0.25, p=0.56, n=4 rats; mean±s.e.m; 2-sample t-test). Optical HFS (120 Hz, 5 ms pulse width) or LFS (20 Hz, 5 ms pulse width) of the STN expressing CaMKIIα::ChR2-mCherry in 6-OHDA rats did not affect path length (cm/min; HFS vs. light off: 803.82±129.04 vs. 851.95±166.20, p=0.83, n=5 rats; LFS vs. light off: 847.15±141.95 vs. 779.11±104.01, p=0.74, n=2 rats; mean±s.e.m; 2-sample t-test) or head position bias (% of time to the right; HFS vs. light off: 93.97±3.78 vs. 94.20±2.96, p=0.96, n=5 rats; LFS vs. light off: 98.50±1.50 vs. 98.50±0.50, p=1.00, n=rats; mean±s.e.m; 2-sample t-test). 473 nm illumination of the STN expressing GFAP::ChR2-mCherry in 6-OHDA rats also did not affect path length (cm/min; light on vs. light off: 1042.52±113.73 vs. 1025.47±113.63, p=0.92, n=4 rats; mean±s.e.m; 2-sample t-test) or head position bias (% of time to the right; light on vs. light off: 98.16±0.98 vs. 98.98±0.65, p=0.52, n=4 rats; mean±s.e.m; 2-sample t-test).

Light transmission measurements were conducted with blocks of brain tissue prepared from two 300 g Fisher rats and immediately tested. Blocks of tissue 2 mm in thickness were cut in 0-4° C. sucrose solution using a vibratome. The tissue was then placed in a Petri dish containing the same sucrose solution over the photodetector of a power meter. The tip of a 200 μm diameter optical fiber coupled to a blue or yellow diode laser (473 nm or 561 nm, 30 mW fiber output) was mounted on a micromanipulator. First, the power was measured through the solution. Then, the tip of the fiber was moved down into the tissue in 100 μm increments and the power was measured. When the fiber reached the Petri dish, the power measured was compared to the initial measurement through the solution to confirm the total power output through the fiber. The percent transmission fraction was then calculated as the ratio between the power measured through tissue and the power measured through solution. The power intensity was then calculated by considering the light intensity spread due to the conical shape of the 30 mW light output from a 400 μm fiber based on the fiber's numerical aperture of 0.37. The fiber output was assumed to be uniform across the diameter of the cone. Measurements were made through grey matter in three blocks of brain tissue for each wavelength with one block each moving anterior-posterior in the thalamus and in the cortex and dorsal-ventral through the thalamus.

Threshold search in Clampfit was used for automated detection of spikes in the multi-unit recording, which was then validated by visual inspection; the spike waveforms displayed by Clampfit were observed to check the quality of spike detection. For traces with multiple spike populations, thresholds were set to capture all the spikes; during bursting, it is likely that multiple neurons were recorded from simultaneously. Bursts were identified in Clampfit; any two consecutive spikes occurring in an interval less than 300 ms were counted as belonging to the same burst and only bursts of at least 3 spikes were included. To quantify the neural activity at different frequencies, spectra for in vivo extracellular recording traces were generated using a wavelet transform after converting the traces into binary spike trains. The trace was then converted into a histogram with a binwidth of 0.5 ms for each of the duration-matched pre-stimulation, stimulation, and post-stimulation epochs. The start and end times for each of the segments, as well as the number of spikes, are listed below.

TABLE 1

The three segments of each power spectra were time matched; this table shows the segments of each trace (the start and end time in seconds), as well as the number of spikes detected during each period. Time intervals were chosen to reflect stationary states before, during, and after stimulation for each trace, to account for temporal delays in onset or offset of physiological effects.

Figure 13:
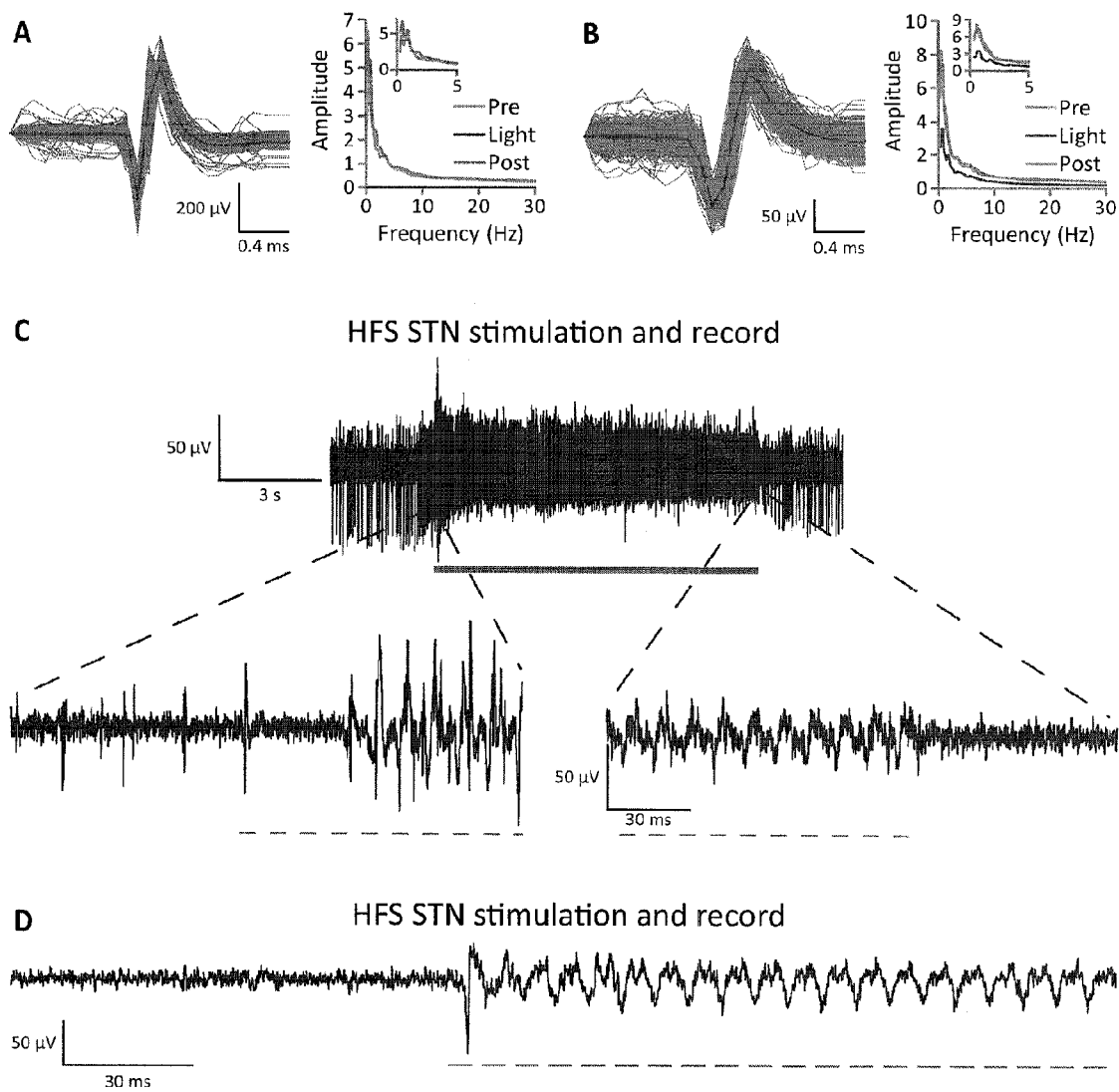
FIG. 13A-D shows additional electrophysiological results.

| | Pre-Stimulation | | | Light On | | | Post-Stimulation | | |
|---|---|---|---|---|---|---|---|---|---|
| | Start | End | Spikes | Start | End | Spikes | Start | End | Spikes |
| FIG. 4 (CaMKIIα::eNpHR) | 32.5 | 72.5 | 413 | 102.5 | 142.5 | 84 | 175 | 215 | 435 |
| FIG. 7 (CaMKIIα::ChR2, HFS) | 5.28 | 10.4 | 238 | 15.38 | 20.5 | 477 | 22.48 | 27.6 | 235 |
| FIG. 8 (Thy1::ChR2, HFS) | 0 | 10.62 | 90 | 14.98 | 25.6 | 0 | 29.38 | 40 | 94 |
| FIG. 8 (Thy1::ChR2, LFS) | 0 | 10.62 | 139 | 14.98 | 25.6 | 383 | 29.38 | 40 | 132 |
| FIG. 9 (Thy1, HFS M1, M1 recd) | 0.8 | 4.8 | 55 | 15.46 | 19.46 | 28 | 26 | 30 | 30 |
| FIG. 9 (Thy1, HFS M1, STN recd) | 0.94 | 5.4 | 19 | 15 | 19.46 | 37 | 25.54 | 30 | 16 |
| FIG. 9 (Thy1, LFS M1, M1 recd) | 0 | 5.5 | 131 | 18.5 | 24 | 313 | 30.5 | 36 | 64 |
| FIG. 9 (Thy1, LFS M1, STN recd) | 0 | 5.5 | 50 | 18.5 | 24 | 115 | 30.5 | 36 | 39 |
| FIG. 13 (eNpHR, small unit) | 32.5 | 72.5 | 263 | 102.5 | 142.5 | 84 | 175 | 215 | 248 |
| FIG. 13 (eNpHR, large unit) | 32.5 | 72.5 | 114 | 102.5 | 142.5 | 0 | 175 | 215 | 145 |

The spike histograms were then convolved with a wavelet to measure the amplitude of the spectra at frequencies below 150 Hz over time. The average amplitude over time for each frequency was then plotted. The wavelet used is reproduced below.

$$g(f,t) = e^{-t^2/2\sigma^2} e^{-2\pi i f t}$$

$$\sigma = 4/(3f).$$

For determining the change in activity of multiple frequency bands, amplitude spectra for multiple duration-matched baseline and stimulation sweeps were calculated as described above. Mean amplitude within each frequency band was determined and the ratio of this value (stimulation/baseline) was calculated. Spike latencies of the M1 response to optical stimulation of the STN were determined by measuring the delay between the first peaks in simultaneous optrode recordings of M1 and STN of a Thy1::ChR2-EYFP 6-OHDA mouse. 20 Hz, 5 ms pulse width of 473 nm light was used to activate the STN.

Figure 10:
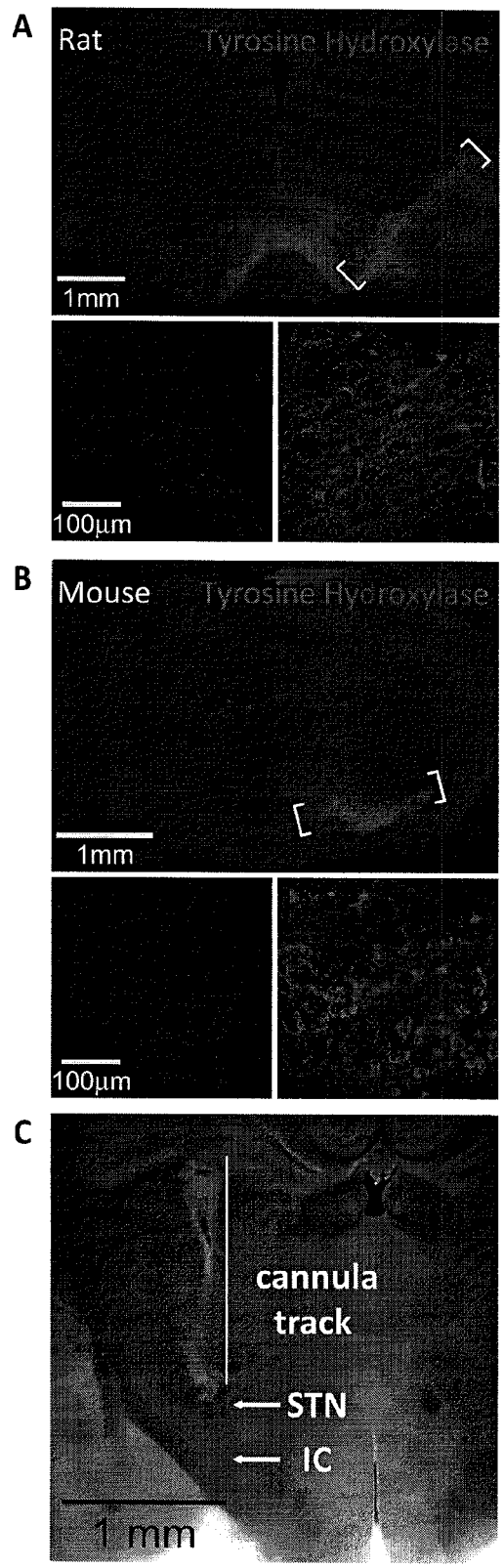
FIG. 10A-C shows substantia nigra lesion and cannula track.

FIG. 10 shows substantia nigra lesion and cannula track. Loss of nigral dopaminergic cells following 6-OHDA administration in rat (A) and mouse (B): coronal slices (rat: AP −5.8; mouse AP −3) show decreased tyrosine hydroxylase levels (red) unilaterally in the substantia nigra pars compacta; SNc is outlined by white brackets. Insets below show higher resolution images of the lesioned (left) and unlesioned (right) sides of the substantia nigra. (C) Cannula track is visible in a coronal slice showing correct placement of the cannula above the STN area.

Figure 11:
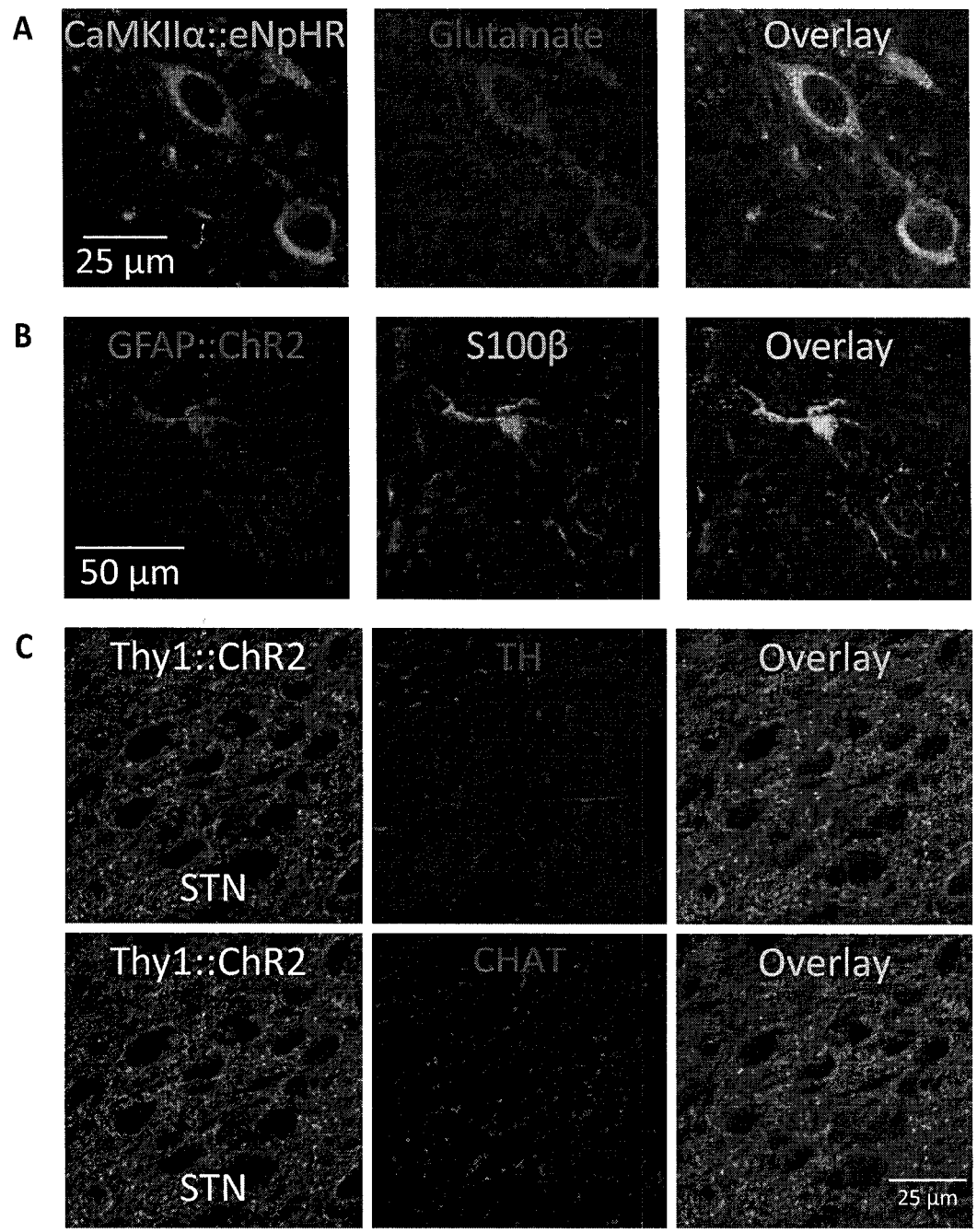
FIG. 11A-C shows an additional histological characterization.

FIG. 11 shows an additional histological characterization. (A) STN cells expressing CaMKIIα::eNpHR-EYFP (green) label for the excitatory neuron specific glutamate marker (red). (B) STN cells expressing GFAP::ChR2-mCherry (red) costain with the astroglia-specific marker S100β (green). In both (A) and (B) yellow indicates colocalization of the two markers. (C) Representative confocal images of TH stain for dopamine (top) and CHAT stain for acetylcholine (bottom) showed no colocalization with Thy1::ChR2-EYFP expression in the STN.

Figure 12:
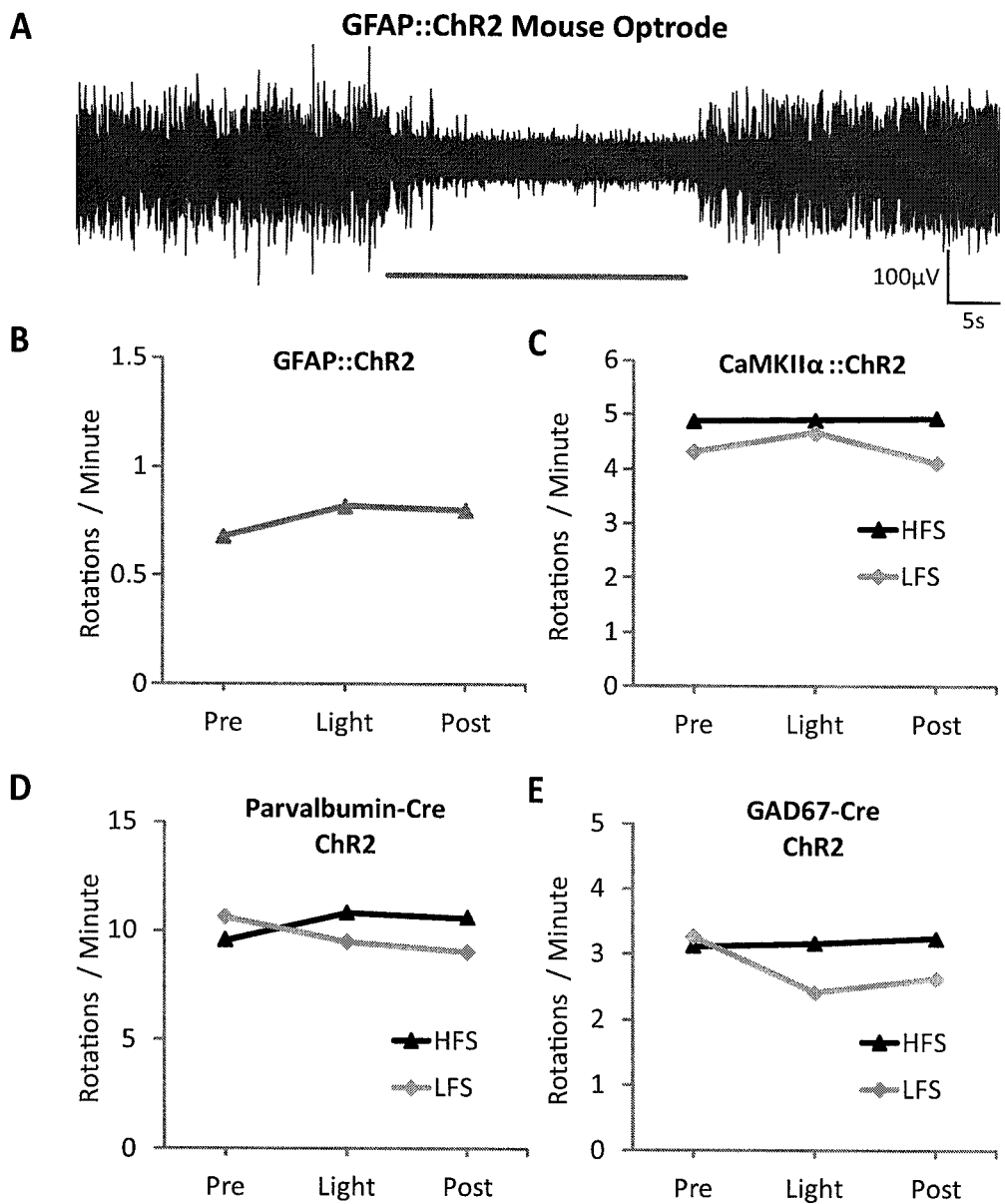
FIG. 12A-D shows additional behavioral results.

FIG. 12 shows additional behavioral results. (A) Continuous 473 nm illumination of the STN expressing GFAP::ChR2-mCherry in an anesthetized 6-OHDA mouse completely inhibited STN activity. (B) and (C): Extension of mouse results. (B) Amphetamine-induced rotations were not affected by 50% duty cycle illumination of the GFAP::ChR2 expressing STN in 6-OHDA mice (n=1 mouse and 2 sessions). (C) Amphetamine-induced rotations were not affected by high (130 Hz, 5 ms pulse width, n=1 mouse and 2 sessions) or low (20 Hz, 5 ms, n=1 mouse and 1 session) frequency optical stimulation in the CaMKIIα::ChR2 expressing STN in 6-OHDA mice. (D) and (C): Modulation of inhibitory neurons during behavior. Although mainly excitatory, STN has about 7-10% percent cells that stain for inhibitory neuronal markers, such as GAD65/67 and parvalbumin (Allen Brain Atlas). To obtain specific expression in either GAD67 or parvalbumin neurons we injected GAD67-Cre and parvalbumin-Cre mice respectively (gift of Sylvia Arber) with a Cre-inducible adeno-associated virus (AAV) vector carrying ChR2-EYFP (Methods). Cre-dependent opsin expression was observed in the STN region, but behavior was unchanged with optical stimulation. (D) Amphetamine-induced rotations were not affected by high (130 Hz, 5 ms, n=2 mice and 4 sessions) or low (20 Hz, 5 ms, n=1 mouse and 2 sessions) frequency optical stimulation in 6-OHDA GAD67-Cre mice. (E) Amphetamine-induced rotations were not affected by high (130 Hz, 5 ms, n=2 mice and 2 sessions) or low (20 Hz, 5 ms, n=2 mice and 2 sessions) frequency optical stimulation in 6-OHDA parvalbumin-Cre mice.

FIG. 13 shows additional electrophysiological results. Isolation of large amplitude (A) and small amplitude (B) units from the trace in FIG. 4C and corresponding power spectra. Red lines represent average waveforms for all superimposed spikes that occurred during 70s of baseline activity (n=205 spikes for large amplitude unit and n 428 spikes for small amplitude unit). Both small and large amplitude units showed decreased activity during light that returned to normal baseline levels after stimulation. (C) Response of STN to optical stimulation of STN in a Thy1::ChR2-EYFP 6-OHDA mouse at 90 Hz. The STN is initially excited but activity is reduced in the emergent stationary state measured by loss of the large amplitude spikes evident during the baseline; nevertheless, significant low amplitude activity persists throughout the stimulation. (D) High-temporal resolution trace of the STN response to optical stimulation of STN in a Thy1::ChR2-EYFP 6-OHDA mouse at 130 Hz (see FIG. 5B for full trace). Again, the STN initially responds with a spike followed by low amplitude activity throughout stimulation. Changes in amplitude of the local circuit responses can reflect either altered recruited cell number or altered excitability of recruited cellular elements. While optrode recordings cannot report on the precise cell types involved in generating activity, by eliminating the electrical stimulation artifact these recordings provide a window into the amplitude and timing properties of local circuit electrical responses arising from local excitatory or inhibitory cell types and fibers in the STN region that could not be achieved with electrical stimulation.

Figure 14:
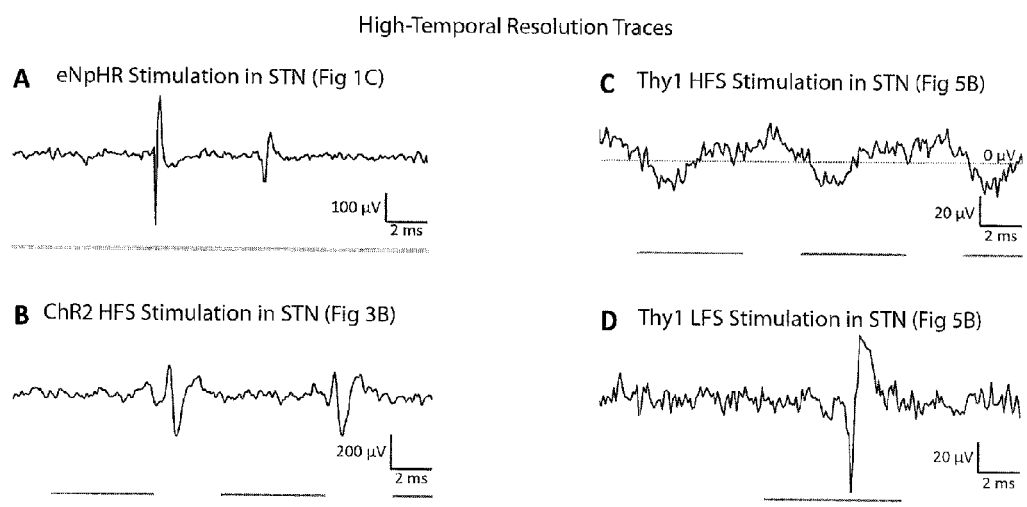
FIG. 14A-D shows high-temporal resolution optrode traces.

FIG. 14 shows high-temporal resolution optrode traces. (A) Single unit activity in CaMKIIα::eNpHR-EYFP expressing STN with continuous 561 nm light illumination in an anesthetized 6-OHDA rat (corresponding to trace in FIG. 4C). (B) Neuronal activity in CaMKIIα::ChR2-mCherry expressing STN with high frequency optical stimulation (120 Hz, 5 ms pulse width, 473 nm) in an anesthetized 6-OHDA rat (corresponding to trace in FIG. 3B). (C) and (D) Activity in the STN region in an anesthetized Thy1::ChR2-EYFP 6-OHDA mouse in response to high (HFS, 130 Hz, 5 ms) and low (LFS, 20 Hz, 5 ms) frequency optical stimulation using 473 nm light. Note the low amplitude of activity in the HFS trace (corresponding to trace in FIG. 5B).

FIG. 15 shows latency of M1 response to optical stimulation of STN. (A) Response of M1 Layer 5 (L5) to optical stimulation of STN in the Thy1::ChR2-EYFP 6-OHDA mouse at 20 Hz, 5 ms pulse width. (B) While stimulating STN with light, simultaneous recordings of light-induced activity in the STN (top trace) and M1/L5 (bottom trace) revealed short latency differences between the first peaks consistent with antidromic spiking. (C) Individual latency differences between the first peak in STN and M1/L5 for 16 stimulation bouts revealed minimal jitter (S.D.=0.032 ms) consistent with antidromic spiking in the well-known M1-STN projection.

Figure 16:
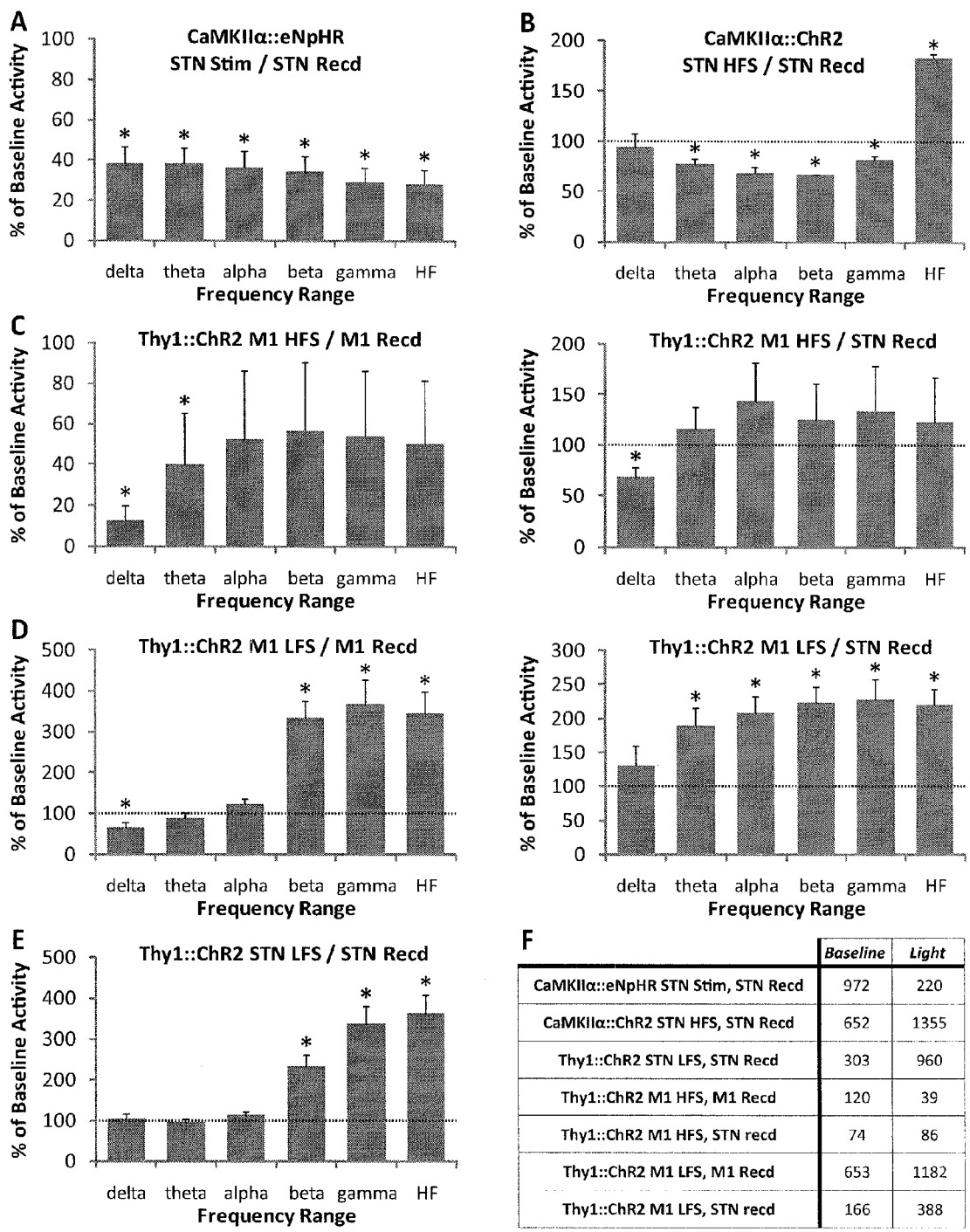
FIG. 16A-F shows changes in frequency characteristics of neuronal activity produced by optical stimulation While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

FIG. 16 shows changes in frequency characteristics of neuronal activity produced by optical stimulation. (A) Activity in all frequency bands was reduced by continuous 561 nm illumination of the STN expressing CaMKIIα::eNpHR-EYFP in anesthetized 6-OHDA rats (n=5 sweeps). Frequency bands are defined as: delta 1-3 Hz; theta 4-8 Hz; alpha 9-12 Hz; beta 13-30 Hz; gamma 31-80 Hz; high frequency (HF) 81-130 Hz. (B) Optical HFS (120 Hz, 5 ms pulse width) of the STN expressing CaMKIIα::ChR2-mCherry in 6-OHDA rats reduced activity for frequencies between 4 and 80 Hz, while increasing activity in the HF band (n=3). (C) Activity change in M1 (left, n=4) and STN (right, n=4) produced by optical HFS (130 Hz, 5 ms) stimulation of M1 in 6-OHDA Thy1::ChR2 mice. Delta activity in both M1 and STN was reduced. (D) Activity change in M1 (left, n=4) and STN (right, n=4)

produced by optical LFS (20 Hz, 5 ms) stimulation of M1 in 6-OHDA Thy1::ChR2 mice. Beta, gamma, and HF activity in both M1 and STN was increased. (E) Optical LFS (20 Hz, 5 ms) of the STN in 6-OHDA Thy1::ChR2 mice increased activity in the beta, gamma, and HF bands (n=3). (F) Spike counts for duration-matched baseline and optical stimulation segments for each experiment type. Optical stimulation of the STN expressing CaMKIIα::GFAP-mCherry and optical HFS in 6-OHDA Thy1::ChR2 mice abolished spiking activity, reducing activity across all frequencies to zero (not shown). Error bars are s.e.m.; t-test with μ=100 used for statistics, *p<0.05.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include additional modifications to VChR1-based sequences. Such modifications and changes do not depart from the true spirit and scope of the present invention, which is set forth in the following claims.

The invention claimed is:

1. A method for modulating the activity of a cell engineered to express a *Volvox carteri* light-responsive ion channel protein (VChR1), the method comprising:
activating the light-responsive VChR1 protein with light.

2. The method of claim 1, wherein the cell is a stem cell.

3. The method of claim 1, wherein the light-responsive VChR1 protein is activated by light having a wavelength in a range of from 535 nm to 589 nm.

4. The method of claim 1, wherein the light-responsive VChR1 protein comprises the amino acid sequence set forth in SEQ ID NO:3.

5. The method of claim 1, wherein the cell is a neuronal cell.

6. The method of claim 5, wherein the light-responsive VChR1 protein is encoded by a nucleotide sequence operably linked to an alpha-CaMKII promoter.

7. The method of claim 1, wherein the light-responsive VChR1 protein is encoded by a nucleotide sequence that is optimized for expression in a mammalian cell.

8. The method of claim 1, wherein the light-responsive VChR1 protein is encoded by an expression vector.

9. The method of claim 8, wherein the expression vector is a viral vector.

10. The method of claim 9, wherein the viral vector is a lentiviral vector or an adenoassociated virus (AAV) vector.

11. The method of claim 1, wherein the cell is further engineered to express a light-responsive ChR2 protein from *Chlamydomonas reinhardtii*.

12. The method of claim 11, wherein the ChR2 protein comprises the amino acid sequence set forth in SEQ ID NO:2.

13. The method of claim 1, wherein the cell is further engineered to express a light-responsive NpHR protein from *Natromonas pharaonis*.

14. The method of claim 1, wherein the ChR2 protein is activated by light having a wavelength of 589 nm

* * * * *

UNITED STATES PATENT AND TRADEMARK OFFICE
CERTIFICATE OF CORRECTION

PATENT NO.        : 8,603,790 B2                                            Page 1 of 1
APPLICATION NO.   : 12/988567
DATED             : December 10, 2013
INVENTOR(S)       : Deisseroth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this

Twenty-third Day of May, 2017

Michelle K. Lee
*Director of the United States Patent and Trademark Office*

SEQUENCE LISTING

<160> NUMBER OF SEQ ID NOS: 3

<210> SEQ ID NO 1
<211> LENGTH: 294
<212> TYPE: PRT
<213> ORGANISM: Artificial Sequence
<220> FEATURE:
<223> OTHER INFORMATION: ChR1 Protein

<400> SEQUENCE: 1

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Ser Ala Leu Cys Leu Met Phe Tyr Gly Tyr Gln Thr Trp
    50                  55                  60

Lys Ser Thr Cys Gly Trp Glu Glu Ile Tyr Val Ala Thr Ile Glu Met
65                  70                  75                  80

Ile Lys Phe Ile Ile Glu Tyr Phe His Glu Phe Asp Glu Pro Ala Val
                85                  90                  95

Ile Tyr Ser Ser Asn Gly Asn Lys Thr Val Trp Leu Arg Tyr Ala Glu
            100                 105                 110

Trp Leu Leu Thr Cys Arg Val Ile Leu Ile His Leu Ser Asn Leu Thr
        115                 120                 125

Gly Leu Ala Asn Asp Tyr Asn Lys Arg Thr Met Gly Leu Leu Val Ser
    130                 135                 140

Asp Ile Gly Thr Ile Val Trp Gly Thr Thr Ala Ala Leu Ser Lys Gly
145                 150                 155                 160

Tyr Val Arg Val Ile Phe Phe Leu Met Gly Leu Cys Tyr Gly Ile Tyr
                165                 170                 175

Thr Phe Phe Asn Ala Ala Lys Val Tyr Ile Glu Ala Tyr His Thr Val
            180                 185                 190

Pro Lys Gly Ile Cys Arg Asp Leu Val Arg Tyr Leu Ala Trp Leu Tyr
        195                 200                 205

Phe Cys Ser Trp Ala Met Phe Pro Val Leu Phe Leu Leu Gly Pro Glu
    210                 215                 220

Gly Phe Gly His Ile Asn Gln Phe Asn Ser Ala Ile Ala His Ala Ile
225                 230                 235                 240

Leu Asp Leu Ala Ser Lys Asn Ala Trp Ser Met Met Gly His Phe Leu
                245                 250                 255

Arg Val Lys Ile His Glu His Ile Leu Leu Tyr Gly Asp Ile Arg Lys
            260                 265                 270
```

```
Lys Gln Lys Val Asn Val Ala Gly Gln Glu Met Glu Val Glu Thr Met
        275                 280                 285

Val His Glu Glu Asp Asp
    290

<210> SEQ ID NO 2
<211> LENGTH: 305
<212> TYPE: PRT
<213> ORGANISM: Artificial Sequence
<220> FEATURE:
<223> OTHER INFORMATION: ChR2 Protein

<400> SEQUENCE: 2

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65              70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu
305

<210> SEQ ID NO 3
<211> LENGTH: 300
```

```
<212> TYPE: PRT
<213> ORGANISM: Artificial Sequence
<220> FEATURE:
<223> OTHER INFORMATION: VChR1

<400> SEQUENCE: 3

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300
```